(12) United States Patent
Hong

(10) Patent No.: US 10,125,362 B2
(45) Date of Patent: Nov. 13, 2018

(54) RNA-INTERFERENCE-INDUCING NUCLEIC ACID MOLECULE ABLE TO PENETRATE INTO CELLS, AND USE THEREFOR

(71) Applicant: OliX Pharmaceuticals, Inc., Seoul (KR)

(72) Inventor: Sun Woo Hong, Suwon-si (KR)

(73) Assignee: OliX Pharmaceuticals, Inc., Seoul (KR)

( * ) Notice: Subject to any disclaimer, the term of this patent is extended or adjusted under 35 U.S.C. 154(b) by 0 days.

(21) Appl. No.: 14/403,121

(22) PCT Filed: May 21, 2013

(86) PCT No.: PCT/KR2013/004463
§ 371 (c)(1),
(2) Date: Nov. 21, 2014

(87) PCT Pub. No.: WO2013/176477
PCT Pub. Date: Nov. 28, 2013

(65) Prior Publication Data
US 2015/0111948 A1  Apr. 23, 2015

(30) Foreign Application Priority Data

May 22, 2012  (KR) .................... 10-2012-0053950

(51) Int. Cl.
*C12N 15/11* (2006.01)
*C12N 15/113* (2010.01)
*C12N 15/87* (2006.01)

(52) U.S. Cl.
CPC .......... *C12N 15/113* (2013.01); *C12N 15/111* (2013.01); *C12N 15/87* (2013.01); *C12N 2310/14* (2013.01); *C12N 2310/313* (2013.01); *C12N 2310/315* (2013.01); *C12N 2310/3515* (2013.01); *C12N 2320/32* (2013.01)

(58) Field of Classification Search
CPC . C12N 15/113; C12N 15/111; C12N 2310/11; C12N 2310/14; C12N 2310/321
See application file for complete search history.

(56) References Cited

U.S. PATENT DOCUMENTS

| | | | |
|---|---|---|---|
| 5,837,258 A | 11/1998 | Grotendorst | |
| 2004/0138163 A1 | 7/2004 | McSwiggen et al. | |
| 2004/0180351 A1* | 9/2004 | Giese | C12N 15/111 435/6.11 |
| 2004/0266707 A1 | 12/2004 | Leake et al. | |
| 2005/0119202 A1 | 6/2005 | Kreutzer et al. | |
| 2006/0069050 A1 | 3/2006 | Rana | |
| 2006/0094032 A1* | 5/2006 | Fougerolles | A61K 31/712 435/6.16 |
| 2006/0105976 A1* | 5/2006 | Soutschek | C12N 15/113 514/44 A |
| 2006/0134787 A1 | 6/2006 | Zamore et al. | |
| 2006/0142228 A1 | 6/2006 | Ford et al. | |
| 2006/0160123 A1 | 7/2006 | Quay | |
| 2007/0218495 A1 | 9/2007 | Birmingham et al. | |
| 2007/0275914 A1* | 11/2007 | Manoharan | A01K 67/0275 514/44 A |
| 2008/0125386 A1 | 5/2008 | Rana et al. | |
| 2009/0004668 A1 | 1/2009 | Chen et al. | |
| 2009/0012022 A1 | 1/2009 | Milner et al. | |
| 2009/0130751 A1 | 5/2009 | Davidson et al. | |
| 2009/0191625 A1* | 7/2009 | Khvorova | C12N 15/111 435/366 |
| 2009/0208564 A1 | 8/2009 | Li et al. | |
| 2010/0197023 A1 | 8/2010 | Leake et al. | |
| 2010/0291681 A1 | 11/2010 | Khvorova et al. | |
| 2011/0054160 A1 | 3/2011 | Manoharan et al. | |
| 2011/0237647 A1 | 9/2011 | Shirasawa et al. | |
| 2011/0237648 A1 | 9/2011 | Khvorova et al. | |
| 2011/0251258 A1 | 10/2011 | Samarsky et al. | |
| 2011/0263680 A1 | 10/2011 | Khvorova et al. | |
| 2011/0269816 A1 | 11/2011 | Kaspar et al. | |

(Continued)

FOREIGN PATENT DOCUMENTS

| | | |
|---|---|---|
| CN | 101835789 A | 9/2010 |
| EP | 2631291 A2 | 8/2013 |

(Continued)

OTHER PUBLICATIONS

Chiu et al., siRNA function in RNAi: A chemical modification analysis, 2003, RNA, vol. 9, pp. 1034-1048.*
*Homo sapiens* connective tissue growth factor (CTGF), mRNA, NM_001901.1, published on Apr. 23, 2016, accessed and retrieved from www.ncbi.nlm.nih.gov on Apr. 21, 2016. total 12 printout pages.*
Ui-Tei et al., Guidelines for the selection of highly effective siRNA sequences for mammalian and chick RNA interference, 2004, Nucleic Acids Research, vol. 32, pp. 936-948.*
*Homo sapiens* connective tissue growth factor (CTGF), mRNA, GenBank No. NM_001901.2, accessed and retrieved from www.ncbi.nlm.nih.gov on Apr. 20, 2017.*
Bolcato-Bellemin, A., et al., "Sticky overhangs enhance siRNA-mediated gene silencing", "Proc. Natl. Aca. Sci. USA", Oct. 3, 2007, pp. 16050-16055, vol. 104, No. 41.

(Continued)

*Primary Examiner* — Dana H Shin
(74) *Attorney, Agent, or Firm* — Morgan, Lewis & Bockius LLP

(57) ABSTRACT

Provided herein are RNAi-inducing double-stranded nucleic acid molecules having cell penetrating ability and targeting mRNA encoding a connective tissue growth factor (CTGF). In certain embodiments, the RNAi-inducing double-stranded nucleic acid molecule comprises a first strand of having a sequence of UCUUCCAGUCGGUAAGCCGC-GAGGGCAGGCC and comprising 4 to 17 phosphorothioate bonds and at least one 2'-O-Me modified nucleotide, as well as a second strand having a sequence of CUUAC-CGACUGGAAGA and comprising at least one phosphorothioate bond and at least one 2'-O-Me modified nucleotide and further comprising a cholesterol moiety covalently attached to its 3' end.

15 Claims, 14 Drawing Sheets

Specification includes a Sequence Listing.

(56) References Cited

U.S. PATENT DOCUMENTS

| | | |
|---|---|---|
| 2012/0016011 A1 | 1/2012 | Pickering et al. |
| 2012/0238017 A1 | 9/2012 | Lee |
| 2013/0115613 A1 | 5/2013 | Madiraju et al. |
| 2013/0123342 A1 | 5/2013 | Brown |
| 2013/0131142 A1* | 5/2013 | Libertine ............ A61K 9/0051 514/44 A |
| 2013/0273657 A1 | 10/2013 | Lee |
| 2013/0317080 A1* | 11/2013 | Rajeev ................ C12N 15/111 514/44 A |
| 2014/0094501 A1 | 4/2014 | Puri et al. |
| 2014/0227266 A1 | 8/2014 | Lee et al. |
| 2014/0350068 A1 | 11/2014 | Feinstein et al. |
| 2017/0298358 A1* | 10/2017 | Lee ........................ A61K 9/007 |

FOREIGN PATENT DOCUMENTS

| | | | |
|---|---|---|---|
| JP | 2008535496 A | 9/2008 | |
| JP | 2011500003 A | 1/2011 | |
| JP | 2011101655 A | 5/2011 | |
| JP | 2012502991 A | 2/2012 | |
| JP | 2012061007 A | 3/2012 | |
| KR | 1020070028363 A | 3/2007 | |
| KR | 10-2009-0065880 A | 6/2009 | |
| WO | WO-02/055693 A2 | 7/2002 | |
| WO | WO-2005/062937 A2 | 7/2005 | |
| WO | WO-2007/022470 A2 | 2/2007 | |
| WO | WO-2007/041282 A2 | 4/2007 | |
| WO | WO-2007/128477 A2 | 11/2007 | |
| WO | WO-2009029688 A2 | 3/2009 | |
| WO | WO-2009078685 A2 | 6/2009 | |
| WO | WO 2010033247 A2 * | 3/2010 | ........... C12N 15/111 |
| WO | WO-2011/108682 A1 | 9/2011 | |
| WO | 2012053741 A2 | 4/2012 | |

OTHER PUBLICATIONS

Hines, L., et al., "Synthetic construct *Homo sapiens* clone FLH019006.01L connective tissue growth factor (CTGF) mRNA, partial cds.", GenBank: Accession No. AY890732, Mar. 21, 2005.
Li, G., et al., "Inhibition of connective tissue growth factor by siRNA prevents liver fibrosis in rats", "The Journal of Gene Medicine", May 2, 2006, pp. 889-900, vol. 8.
Luo, G., et al., "Inhibition of Connective Tissue Growth Factor by Small Interfering RNA Prevents Renal Fibrosis in Rats Undergoing Chronic Allograft Nephropathy", "Transplantation Proceedings", Sep. 2008, pp. 2365-2369, vol. 40.
Sioud, M., et al., "Cationic liposome-mediated delivery of siRNAs in adult mice", "Biochemical and Biophysical Research Communications", Dec. 26, 2003, pp. 1220-1225, vol. 312.
Sisco, M., et al., "Antisense inhibition of connective tissue growth factor (CTGF/CCN2) mRNA limits hypertrophic scarring without affecting wound healing in vivo", "Wound Repair and Regeneration", Sep.-Oct. 2008, pp. 661-673, vol. 16.
Chang et al., "Structural diversity repertoire of gene silencing small interfering RNAs," Nucleic Acid Therapeutics, 21(3):125-31 (2011).
Jeong et al., "siRNA conjugate delivery systems," Bioconjugate Chem, 20:5-14 (2009).
Kore et al., "Chemical modification of synthetic RNAi agents and in vivo delivery techniques," Curr Bioactive Compounds, 4:6-14 (2008).
Raouane et al., "Lipid conjugated oligonucleotides: a useful strategy for delivery," Bioconjugate Chem, 23:1091-104 (2012).
Bushati et al., "MicroRNAs in Neurodegeneration," Current Opin Neurobiol, 18: 292-296 (2008).
Doench et al., "siRNAs Can Function as miRNAs," Gene Dev, 17(4): 438-442 (2003).
Doench et al., "Specificity of MicroRNA Target Selection in Translation Repression," Gene Dev, 18: 504-511 (2004).
Elbashir et al., "Duplexes of 21-nucleotide RNAs Mediate RNA Interference in Cultured Mammalian Cells," Nature, 411: 494-498 (May 24, 2001).
Jang et al., "Gene Delivery From Polymer Scaffolds for Tissue Engineering," Expert Rev Med Devic, 1(1): 127-138 (2004).
Martinez et al., "Singe-Stranded Antisense siRNAs Guide Target RNA Cleavage in RNAi," Cell, 110: 563-574 (Sep. 6, 2002).
Opalinska et al., "Nucleic-acid Therapeutics: Basic Principles and Recent Applications," Nature Rev, 1(7): 503-514 (2002).
Paroo et al., "Challenges for RNAi in vivo," Trends in Biotech, 22(8): 390-394 (2004).
Song et al., "The Crystal Structure of the Argonaute2 PAZ Domain Reveals an RNA Binding Motif in RNAi Effector Complexes," Nat Struct Biol, 10(12): 1026-1032 (Dec. 2003).
Vasdudevan et al., "Switching from Repression to Activation: MicroRNAs Can Up-Regulate Translation," Science, 318: 1931-1934 (2007).
Wang et al., "Nucleation, Propagation and Cleavage of Target RNAs in Ago Silencing Complexes," Nature, 461: 754-762 (Oct. 8, 2009).
Bramsen et al., "Improved Silencing Properties Using Small Internally Segmented Interfering RNAs," Nucleic Acids Res, 35: 5886-5897 (2007).
Caplen et al., "Specific Inhibition of Gene Expression by Small Double-Stranded RNAs in Invertebrate and Vertebrate Systems," Proc Natl Acad Sci USA, 98(17): 9742-9747 (2001).
Chang et al., "Asymmetric Shorter-Duplex siRNA Structures Trigger Efficient Gene Silencing With Reduced Nonspecific Effects," Mol Ther, 17: 725-732 (2009).
Elbashir et al., "Functional Anatomy of siRNAs for Mediating Efficient RNAi in *Drosophila melanogaster* Embryo Lysate," EMBO J, 20(23): 6877-6888 (2001).
Fire et al., "Potent and Specific Genetic Interference by Double-Stranded RNA in Caenorhabditis Elegans," Nature, 391: 806-811 (1998).
Fire,"RNA-triggered Gene Silencing," Trends Genet, 15(9): 358-363 (1999).
Hammond, "Post-Transcriptional Gene Silencing by Double-Stranded RNA," Nature Reviews, 2: 110-119 (2001).
Jackson et al., "Expression Profiling Reveals Off-Target Gene Regulation by RNAi," Nat Biotechnol, 21: 635-637 (2003).
Jo et al., "Selection and optimization of asymmetric siRNA targeting the human c-MET gene," Mol Cells, 32(6): 543-548 (2011).
Kulkarni et al., "Evidence of Off-Target Effects Associated with Long dsRNAs in *Drosophila melanogaster* Cell-Based Assays," Nat Methods, 3: 833-838 (2006).
Rose et al., "Functional Polarity is Introduced by Dicer Processing of Short Substrate RNAs," Nucleic Acids Res, 33: 4140-4156 (2005).
Sharp, "RNA—Interference—2001," Gene Dev, 15: 485-490 (2001).
Soutschek et al., "Therapeutic Silencing of an Endogenous Gene by Systemic Adminstration of Modified siRNAs," Nature, 432: 173-178 (2004).
Ui-Tei et al., "Essential Notes Regarding the Design of Functional siRNAs for Efficient Mammalian RNAi," J Biomed Biotechnol, 2006: 1-8 (2006).
Zamore,"RNA Interference: Listening to the Sound of Silence," Nat Struct Biol, 8(9): 746-750 (2001).

\* cited by examiner

FIG. 3

| No. | NOTATION | SEQ ID No. | | sequence (5'-3') |
|---|---|---|---|---|
| No9 | Chol-lasi-PS(0) | 155 | sense | CUUACCUACUUGAA\*G\*A\*Chol |
| | | 156 | antisense | UCUUCCAGUGUAAGCUCGAGGCAGGCC |
| | Chol-lasi-PS(4) | 157 | sense | CUUACCUACUUGAA\*G\*A\*Chol |
| | | 158 | antisense | UCUUCCAGUGUAAGCUCGAGGCA\*G\*G\*C\*C |
| | Chol-lasi-PS(7) | 159 | sense | CUUACCUACUUGAA\*G\*A\*Chol |
| | | 160 | antisense | UCUUCCAGUGUAAGCUCGAG\*G\*C\*A\*G\*G\*C\*C |
| | Chol-lasi-PS(12) | 161 | sense | CUUACCUACUUGAA\*G\*A\*Chol |
| | | 162 | antisense | UCUUCCAGUGUAAGC\*U\*C\*G\*A\*G\*G\*C\*A\*G\*G\*C\*C |
| | Chol-lasi-PS(17) | 163 | sense | CUUACCUACUUGAA\*G\*A\*Chol |
| | | 164 | antisense | UCUUCCAGUGUAA\*G\*C\*U\*C\*G\*A\*G\*G\*C\*A\*G\*G\*C\*C |
| | Chol-lasi-PS(7)-cy3 | 165 | sense | Cy3\*CUUACCUACUUGAA\*G\*A\*Chol |
| | | 166 | antisense | UCUUCCAGUGUAAGCUCGAGG\*C\*A\*G\*G\*C\*C |

FIG. 6

| ID | SHORT NAME | SEQ ID NO | | Sequence (5'→3') |
|---|---|---|---|---|
| MyD88 | Chol-lasiRNA-PS(7) | 167 | sense | CCAGACCAAAUGUG*C*A*Chol |
| | | 168 | antisense | UGCAAACUUGGUCUGGAAGCGACA*U*G*C*C*U*U*g | though a composition of delivery vehicles, thus inducing toxicity.

```
                           SEQUENCE LISTING

<160> NUMBER OF SEQ ID NOS: 182

<210> SEQ ID NO 1
<211> LENGTH: 21
<212> TYPE: DNA
<213> ORGANISM: Artificial
<220> FEATURE:
<223> OTHER INFORMATION: antisense strand of CTGF siRNA No.12

<400> SEQUENCE: 1
gcgaggagug ggugugugat t                                            21

<210> SEQ ID NO 2
<211> LENGTH: 21
<212> TYPE: DNA
<213> ORGANISM: Artificial
<220> FEATURE:
<223> OTHER INFORMATION: antisense strand of CTGF siRNA No.1

<400> SEQUENCE: 2
uccucgcagc auuucccggt t                                            21

<210> SEQ ID NO 3
<211> LENGTH: 16
<212> TYPE: DNA
<213> ORGANISM: Artificial
<220> FEATURE:
<223> OTHER INFORMATION: sense strand of CTGF asiRNA No.1

<400> SEQUENCE: 3
aggagugggu guguga                                                  16

<210> SEQ ID NO 4
<211> LENGTH: 21
<212> TYPE: DNA
<213> ORGANISM: Artificial
<220> FEATURE:
<223> OTHER INFORMATION: antisense strand of CTGF asiRNA No.1

<400> SEQUENCE: 4
uccucgcagc auuucccggt t                                            21

<210> SEQ ID NO 5
<211> LENGTH: 16
<212> TYPE: DNA
<213> ORGANISM: Artificial
<220> FEATURE:
<223> OTHER INFORMATION: sense strand of CTGF lasiRNA No.1

<400> SEQUENCE: 5
aggagugggu guguga                                                  16

<210> SEQ ID NO 6
<211> LENGTH: 31
<212> TYPE: DNA
<213> ORGANISM: Artificial
<220> FEATURE:
<223> OTHER INFORMATION: antisense strand of CTGF lasiRNA No.1

<400> SEQUENCE: 6
```
ucacacaccc acuccucgca gcauuucccg g         31

<210> SEQ ID NO 7
<211> LENGTH: 21
<212> TYPE: DNA
<213> ORGANISM: Artificial
<220> FEATURE:
<223> OTHER INFORMATION: sense strand of CTGF siRNA No.2

<400> SEQUENCE: 7
agaccugugg gaugggcaut t         21

<210> SEQ ID NO 8
<211> LENGTH: 21
<212> TYPE: DNA
<213> ORGANISM: Artificial
<220> FEATURE:
<223> OTHER INFORMATION: antisense strand of CTGF siRNA No.2

<400> SEQUENCE: 8
caggucuugg aacaggcgct t         21

<210> SEQ ID NO 9
<211> LENGTH: 16
<212> TYPE: DNA
<213> ORGANISM: Artificial
<220> FEATURE:
<223> OTHER INFORMATION: antisense strand of CTGF asiRNA No.2

<400> SEQUENCE: 9
ccugugggau gggcau         16

<210> SEQ ID NO 10
<211> LENGTH: 21
<212> TYPE: DNA
<213> ORGANISM: Artificial
<220> FEATURE:
<223> OTHER INFORMATION: antisense strand of CTGF asiRNA No.2

<400> SEQUENCE: 10
caggucuugg aacaggcgct t         21

<210> SEQ ID NO 11
<211> LENGTH: 16
<212> TYPE: DNA
<213> ORGANISM: Artificial
<220> FEATURE:
<223> OTHER INFORMATION: sense strand of CTGF lasiRNA No.2

<400> SEQUENCE: 11
ccugugggau gggcau         16

<210> SEQ ID NO 12
<211> LENGTH: 31
<212> TYPE: DNA
<213> ORGANISM: Artificial
<220> FEATURE:
<223> OTHER INFORMATION: antisense strand of CTGF lasiRNA No.2

<400> SEQUENCE: 12
augcccaucc cacaggucuu ggaacaggcg c         31

<210> SEQ ID NO 13
<211> LENGTH: 21
<212> TYPE: DNA
<213> ORGANISM: Artificial

```
<220> FEATURE:
<223> OTHER INFORMATION: sense strand of CTGF siRNA No.3

<400> SEQUENCE: 13
acaggaagau guacggagat t                                              21

<210> SEQ ID NO 14
<211> LENGTH: 21
<212> TYPE: DNA
<213> ORGANISM: Artificial
<220> FEATURE:
<223> OTHER INFORMATION: antisense strand of CTGF siRNA No.3

<400> SEQUENCE: 14
uuccuguagu acagcgauut t                                              21

<210> SEQ ID NO 15
<211> LENGTH: 16
<212> TYPE: DNA
<213> ORGANISM: Artificial
<220> FEATURE:
<223> OTHER INFORMATION: sense strand of CTGF asiRNA No.3

<400> SEQUENCE: 15
ggaagaugua cggaga                                                    16

<210> SEQ ID NO 16
<211> LENGTH: 21
<212> TYPE: DNA
<213> ORGANISM: Artificial
<220> FEATURE:
<223> OTHER INFORMATION: antisense strand of CTGF asiRNA No.3

<400> SEQUENCE: 16
uuccuguagu acagcgauut t                                              21

<210> SEQ ID NO 17
<211> LENGTH: 16
<212> TYPE: DNA
<213> ORGANISM: Artificial
<220> FEATURE:
<223> OTHER INFORMATION: sense strand of CTGF lasiRNA No.3

<400> SEQUENCE: 17
ggaagaugua cggaga                                                    16

<210> SEQ ID NO 18
<211> LENGTH: 31
<212> TYPE: DNA
<213> ORGANISM: Artificial
<220> FEATURE:
<223> OTHER INFORMATION: antisense strand of CTGF lasiRNA No.3

<400> SEQUENCE: 18
ucuccguaca ucuuccugua guacagcgau u                                   31

<210> SEQ ID NO 19
<211> LENGTH: 21
<212> TYPE: DNA
<213> ORGANISM: Artificial
<220> FEATURE:
<223> OTHER INFORMATION: sense strand of CTGF siRNA No.4

<400> SEQUENCE: 19
gcaccagcau gaagacauat t                                              21
```

<210> SEQ ID NO 20
<211> LENGTH: 21
<212> TYPE: DNA
<213> ORGANISM: Artificial
<220> FEATURE:
<223> OTHER INFORMATION: antisense strand of CTGF siRNA No.4

<400> SEQUENCE: 20
uaugucuuca ugcuggugct t                                                    21

<210> SEQ ID NO 21
<211> LENGTH: 16
<212> TYPE: DNA
<213> ORGANISM: Artificial
<220> FEATURE:
<223> OTHER INFORMATION: sense strand of CTGF asiRNA No.4

<400> SEQUENCE: 21
ccagcaugaa gacaua                                                          16

<210> SEQ ID NO 22
<211> LENGTH: 21
<212> TYPE: DNA
<213> ORGANISM: Artificial
<220> FEATURE:
<223> OTHER INFORMATION: antisense strand of CTGF asiRNA No.4

<400> SEQUENCE: 22
uaugucuuca ugcuggugct t                                                    21

<210> SEQ ID NO 23
<211> LENGTH: 16
<212> TYPE: DNA
<213> ORGANISM: Artificial
<220> FEATURE:
<223> OTHER INFORMATION: sense strand of CTGF lasiRNA No.4

<400> SEQUENCE: 23
ccagcaugaa gacaua                                                          16

<210> SEQ ID NO 24
<211> LENGTH: 31
<212> TYPE: DNA
<213> ORGANISM: Artificial
<220> FEATURE:
<223> OTHER INFORMATION: antisense strand of CTGF lasiRNA No.4

<400> SEQUENCE: 24
uaugucuuca ugcuggucca gccagaaagc u                                         31

<210> SEQ ID NO 25
<211> LENGTH: 21
<212> TYPE: DNA
<213> ORGANISM: Artificial
<220> FEATURE:
<223> OTHER INFORMATION: sense strand of CTGF siRNA No.5

<400> SEQUENCE: 25
gaagacauac cgagcuaaat t                                                    21

<210> SEQ ID NO 26
<211> LENGTH: 21
<212> TYPE: DNA
<213> ORGANISM: Artificial
<220> FEATURE:
<223> OTHER INFORMATION: antisense strand of CTGF siRNA No.5

```
<400> SEQUENCE: 26
uuuagcucgg uaugucuuct t                                              21

<210> SEQ ID NO 27
<211> LENGTH: 16
<212> TYPE: DNA
<213> ORGANISM: Artificial
<220> FEATURE:
<223> OTHER INFORMATION: sense strand of CTGF asiRNA No.5

<400> SEQUENCE: 27
gacauaccga gcuaaa                                                    16

<210> SEQ ID NO 28
<211> LENGTH: 21
<212> TYPE: DNA
<213> ORGANISM: Artificial
<220> FEATURE:
<223> OTHER INFORMATION: antisense strand of CTGF asiRNA No.5

<400> SEQUENCE: 28
uuuagcucgg uaugucuuct t                                              21

<210> SEQ ID NO 29
<211> LENGTH: 16
<212> TYPE: DNA
<213> ORGANISM: Artificial
<220> FEATURE:
<223> OTHER INFORMATION: sense strand of CTGF lasiRNA No.5

<400> SEQUENCE: 29
gacauaccga gcuaaa                                                    16

<210> SEQ ID NO 30
<211> LENGTH: 31
<212> TYPE: DNA
<213> ORGANISM: Artificial
<220> FEATURE:
<223> OTHER INFORMATION: antisense strand of CTGF lasiRNA No.5

<400> SEQUENCE: 30
uuuagcucgg uaugucuuca ugcuggugca g                                   31

<210> SEQ ID NO 31
<211> LENGTH: 21
<212> TYPE: DNA
<213> ORGANISM: Artificial
<220> FEATURE:
<223> OTHER INFORMATION: sense strand of CTGF siRNA No.6

<400> SEQUENCE: 31
gcuaaauucu guggaguaut t                                              21

<210> SEQ ID NO 32
<211> LENGTH: 21
<212> TYPE: DNA
<213> ORGANISM: Artificial
<220> FEATURE:
<223> OTHER INFORMATION: antisense strand of CTGF siRNA No.6

<400> SEQUENCE: 32
auacuccaca gaauuuagct t                                              21

<210> SEQ ID NO 33
```

-continued

```
<211> LENGTH: 16
<212> TYPE: DNA
<213> ORGANISM: Artificial
<220> FEATURE:
<223> OTHER INFORMATION: sense strand of CTGF asiRNA No.6

<400> SEQUENCE: 33
aaauucugug gaguau                                                         16

<210> SEQ ID NO 34
<211> LENGTH: 21
<212> TYPE: DNA
<213> ORGANISM: Artificial
<220> FEATURE:
<223> OTHER INFORMATION: antisense strand of CTGF asiRNA No.6

<400> SEQUENCE: 34
auacuccaca gaauuuagct t                                                   21

<210> SEQ ID NO 35
<211> LENGTH: 16
<212> TYPE: DNA
<213> ORGANISM: Artificial
<220> FEATURE:
<223> OTHER INFORMATION: sense strand of CTGF lasiRNA No.6

<400> SEQUENCE: 35
aaauucugug gaguau                                                         16

<210> SEQ ID NO 36
<211> LENGTH: 31
<212> TYPE: DNA
<213> ORGANISM: Artificial
<220> FEATURE:
<223> OTHER INFORMATION: antisense strand of CTGF lasiRNA No.6

<400> SEQUENCE: 36
auacuccaca gaauuuagcu cgguaugucu u                                        31

<210> SEQ ID NO 37
<211> LENGTH: 21
<212> TYPE: DNA
<213> ORGANISM: Artificial
<220> FEATURE:
<223> OTHER INFORMATION: sense strand of CTGF siRNA No.7

<400> SEQUENCE: 37
gcgaggucau gaagaagaat t                                                   21

<210> SEQ ID NO 38
<211> LENGTH: 21
<212> TYPE: DNA
<213> ORGANISM: Artificial
<220> FEATURE:
<223> OTHER INFORMATION: antisense strand of CTGF siRNA No.7

<400> SEQUENCE: 38
uuguucuuca ugaccucgct t                                                   21

<210> SEQ ID NO 39
<211> LENGTH: 16
<212> TYPE: DNA
<213> ORGANISM: Artificial
<220> FEATURE:
<223> OTHER INFORMATION: sense strand of CTGF asiRNA No.7

<400> SEQUENCE: 39
```

```
aggucaugaa gaagaa                                                     16

<210> SEQ ID NO 40
<211> LENGTH: 21
<212> TYPE: DNA
<213> ORGANISM: Artificial
<220> FEATURE:
<223> OTHER INFORMATION: antisense strand of CTGF asiRNA No.7

<400> SEQUENCE: 40
uuguucuuca ugaccucgct t                                               21

<210> SEQ ID NO 41
<211> LENGTH: 16
<212> TYPE: DNA
<213> ORGANISM: Artificial
<220> FEATURE:
<223> OTHER INFORMATION: sense strand of CTGF lasiRNA No.7

<400> SEQUENCE: 41
aggucaugaa gaagaa                                                     16

<210> SEQ ID NO 42
<211> LENGTH: 31
<212> TYPE: DNA
<213> ORGANISM: Artificial
<220> FEATURE:
<223> OTHER INFORMATION: antisense strand of CTGF lasiRNA No.7

<400> SEQUENCE: 42
uuguucuuca ugaccucgcc gucagggcac u                                    31

<210> SEQ ID NO 43
<211> LENGTH: 21
<212> TYPE: DNA
<213> ORGANISM: Artificial
<220> FEATURE:
<223> OTHER INFORMATION: sense strand of CTGF siRNA No.8

<400> SEQUENCE: 43
uggaagagaa cauuaagaat t                                               21

<210> SEQ ID NO 44
<211> LENGTH: 21
<212> TYPE: DNA
<213> ORGANISM: Artificial
<220> FEATURE:
<223> OTHER INFORMATION: antisense strand of CTGF siRNA No.8

<400> SEQUENCE: 44
uucuuaaugu ucucuuccat t                                               21

<210> SEQ ID NO 45
<211> LENGTH: 16
<212> TYPE: DNA
<213> ORGANISM: Artificial
<220> FEATURE:
<223> OTHER INFORMATION: sense strand of CTGF asiRNA No.8

<400> SEQUENCE: 45
aagagaacau uaagaa                                                     16

<210> SEQ ID NO 46
<211> LENGTH: 21
<212> TYPE: DNA
```

```
<213> ORGANISM: Artificial
<220> FEATURE:
<223> OTHER INFORMATION: antisense strand of CTGF asiRNA No.8

<400> SEQUENCE: 46
uucuuaaugu ucucuuccat t                                        21

<210> SEQ ID NO 47
<211> LENGTH: 16
<212> TYPE: DNA
<213> ORGANISM: Artificial
<220> FEATURE:
<223> OTHER INFORMATION: sense strand of CTGF lasiRNA No.8

<400> SEQUENCE: 47
aagagaacau uaagaa                                              16

<210> SEQ ID NO 48
<211> LENGTH: 31
<212> TYPE: DNA
<213> ORGANISM: Artificial
<220> FEATURE:
<223> OTHER INFORMATION: antisense strand of CTGF lasiRNA No.8

<400> SEQUENCE: 48
uucuuaaugu ucucuuccag gucagcuucg c                             31

<210> SEQ ID NO 49
<211> LENGTH: 21
<212> TYPE: DNA
<213> ORGANISM: Artificial
<220> FEATURE:
<223> OTHER INFORMATION: sense strand of CTGF siRNA No.9

<400> SEQUENCE: 49
cggcuuaccg acuggaagat t                                        21

<210> SEQ ID NO 50
<211> LENGTH: 21
<212> TYPE: DNA
<213> ORGANISM: Artificial
<220> FEATURE:
<223> OTHER INFORMATION: antisense strand of CTGF siRNA No.9

<400> SEQUENCE: 50
ucuuccaguc gguaagccgt t                                        21

<210> SEQ ID NO 51
<211> LENGTH: 16
<212> TYPE: DNA
<213> ORGANISM: Artificial
<220> FEATURE:
<223> OTHER INFORMATION: sense strand of CTGF asiRNA No.9

<400> SEQUENCE: 51
cuuaccgacu ggaaga                                              16

<210> SEQ ID NO 52
<211> LENGTH: 21
<212> TYPE: DNA
<213> ORGANISM: Artificial
<220> FEATURE:
<223> OTHER INFORMATION: antisense strand of CTGF asiRNA No.9

<400> SEQUENCE: 52
ucuuccaguc gguaagccgt t                                        21
```

```
<210> SEQ ID NO 53
<211> LENGTH: 16
<212> TYPE: DNA
<213> ORGANISM: Artificial
<220> FEATURE:
<223> OTHER INFORMATION: sense strand of CTGF lasiRNA No.9

<400> SEQUENCE: 53
cuuaccgacu ggaaga                                                       16

<210> SEQ ID NO 54
<211> LENGTH: 31
<212> TYPE: DNA
<213> ORGANISM: Artificial
<220> FEATURE:
<223> OTHER INFORMATION: antisense strand of CTGF lasiRNA No.9

<400> SEQUENCE: 54
ucuuccaguc gguaagccgc gagggcaggc c                                      31

<210> SEQ ID NO 55
<211> LENGTH: 21
<212> TYPE: DNA
<213> ORGANISM: Artificial
<220> FEATURE:
<223> OTHER INFORMATION: sense strand of CTGF siRNA No.10

<400> SEQUENCE: 55
gcaugaagcc agagagugat t                                                 21

<210> SEQ ID NO 56
<211> LENGTH: 21
<212> TYPE: DNA
<213> ORGANISM: Artificial
<220> FEATURE:
<223> OTHER INFORMATION: antisense strand of CTGF siRNA No.10

<400> SEQUENCE: 56
ucacucucug gcuucaugct t                                                 21

<210> SEQ ID NO 57
<211> LENGTH: 16
<212> TYPE: DNA
<213> ORGANISM: Artificial
<220> FEATURE:
<223> OTHER INFORMATION: sense strand of CTGF asiRNA No.10

<400> SEQUENCE: 57
ugaagccaga gaguga                                                       16

<210> SEQ ID NO 58
<211> LENGTH: 21
<212> TYPE: DNA
<213> ORGANISM: Artificial
<220> FEATURE:
<223> OTHER INFORMATION: antisense strand of CTGF asiRNA No.10

<400> SEQUENCE: 58
ucacucucug gcuucaugct t                                                 21

<210> SEQ ID NO 59
<211> LENGTH: 16
<212> TYPE: DNA
<213> ORGANISM: Artificial
<220> FEATURE:
```

<223> OTHER INFORMATION: sense strand of CTGF lasiRNA No.10

<400> SEQUENCE: 59
ugaagccaga gaguga                                                          16

<210> SEQ ID NO 60
<211> LENGTH: 31
<212> TYPE: DNA
<213> ORGANISM: Artificial
<220> FEATURE:
<223> OTHER INFORMATION: antisense strand of CTGF lasiRNA No.10

<400> SEQUENCE: 60
ucacucucug gcuucaugcc caugucuccg u                                          31

<210> SEQ ID NO 61
<211> LENGTH: 21
<212> TYPE: DNA
<213> ORGANISM: Artificial
<220> FEATURE:
<223> OTHER INFORMATION: sense strand of CTGF siRNA No.10

<400> SEQUENCE: 61
caccauaggu agaauguaat t                                                     21

<210> SEQ ID NO 62
<211> LENGTH: 21
<212> TYPE: DNA
<213> ORGANISM: Artificial
<220> FEATURE:
<223> OTHER INFORMATION: antisense strand of CTGF siRNA No.10

<400> SEQUENCE: 62
uuacauucua ccuaggugt t                                                      21

<210> SEQ ID NO 63
<211> LENGTH: 16
<212> TYPE: DNA
<213> ORGANISM: Artificial
<220> FEATURE:
<223> OTHER INFORMATION: sense strand of CTGF asiRNA No.10

<400> SEQUENCE: 63
cauagguaga auguaa                                                           16

<210> SEQ ID NO 64
<211> LENGTH: 21
<212> TYPE: DNA
<213> ORGANISM: Artificial
<220> FEATURE:
<223> OTHER INFORMATION: antisense strand of CTGF asiRNA No.10

<400> SEQUENCE: 64
uuacauucua ccuaggugt t                                                      21

<210> SEQ ID NO 65
<211> LENGTH: 16
<212> TYPE: DNA
<213> ORGANISM: Artificial
<220> FEATURE:
<223> OTHER INFORMATION: sense strand of CTGF lasiRNA No.10

<400> SEQUENCE: 65
cauagguaga auguaa                                                           16

<210> SEQ ID NO 66
<211> LENGTH: 31
<212> TYPE: DNA
<213> ORGANISM: Artificial
<220> FEATURE:
<223> OTHER INFORMATION: antisense strand of CTGF lasiRNA No.10

<400> SEQUENCE: 66
uuacauucua ccuauggugu ucagaaauug a					31

<210> SEQ ID NO 67
<211> LENGTH: 21
<212> TYPE: DNA
<213> ORGANISM: Artificial
<220> FEATURE:
<223> OTHER INFORMATION: sense strand of CTGF siRNA No.11

<400> SEQUENCE: 67
ccugcaggcu agagaagcat t					21

<210> SEQ ID NO 68
<211> LENGTH: 21
<212> TYPE: DNA
<213> ORGANISM: Artificial
<220> FEATURE:
<223> OTHER INFORMATION: antisense strand of CTGF siRNA No.11

<400> SEQUENCE: 68
ugcuucucua gccugcaggt t					21

<210> SEQ ID NO 69
<211> LENGTH: 16
<212> TYPE: DNA
<213> ORGANISM: Artificial
<220> FEATURE:
<223> OTHER INFORMATION: sense strand of CTGF asiRNA No.11

<400> SEQUENCE: 69
gcaggcuaga gaagca					16

<210> SEQ ID NO 70
<211> LENGTH: 21
<212> TYPE: DNA
<213> ORGANISM: Artificial
<220> FEATURE:
<223> OTHER INFORMATION: antisense strand of CTGF asiRNA No.11

<400> SEQUENCE: 70
ugcuucucua gccugcaggt t					21

<210> SEQ ID NO 71
<211> LENGTH: 16
<212> TYPE: DNA
<213> ORGANISM: Artificial
<220> FEATURE:
<223> OTHER INFORMATION: sense strand of CTGF lasiRNA No.11

<400> SEQUENCE: 71
gcaggcuaga gaagca					16

<210> SEQ ID NO 72
<211> LENGTH: 31
<212> TYPE: DNA
<213> ORGANISM: Artificial
<220> FEATURE:
<223> OTHER INFORMATION: antisense strand of CTGF lasiRNA No.11

```
<400> SEQUENCE: 72
ugcuucucua gccugcagga ggcguuguca u                                    31

<210> SEQ ID NO 73
<211> LENGTH: 21
<212> TYPE: DNA
<213> ORGANISM: Artificial
<220> FEATURE:
<223> OTHER INFORMATION: sense strand of CTGF siRNA No.13

<400> SEQUENCE: 73
ccagagagug agagacauut t                                               21

<210> SEQ ID NO 74
<211> LENGTH: 21
<212> TYPE: DNA
<213> ORGANISM: Artificial
<220> FEATURE:
<223> OTHER INFORMATION: antisense strand of CTGF siRNA No.13

<400> SEQUENCE: 74
aaugucucuc acucucuggt t                                               21

<210> SEQ ID NO 75
<211> LENGTH: 16
<212> TYPE: DNA
<213> ORGANISM: Artificial
<220> FEATURE:
<223> OTHER INFORMATION: sense strand of CTGF asiRNA No.13

<400> SEQUENCE: 75
gagagugaga gacauu                                                     16

<210> SEQ ID NO 76
<211> LENGTH: 21
<212> TYPE: DNA
<213> ORGANISM: Artificial
<220> FEATURE:
<223> OTHER INFORMATION: antisense strand of CTGF asiRNA No.13

<400> SEQUENCE: 76
aaugucucuc acucucuggt t                                               21

<210> SEQ ID NO 77
<211> LENGTH: 16
<212> TYPE: DNA
<213> ORGANISM: Artificial
<220> FEATURE:
<223> OTHER INFORMATION: sense strand of CTGF lasiRNA No.13

<400> SEQUENCE: 77
gagagugaga gacauu                                                     16

<210> SEQ ID NO 78
<211> LENGTH: 31
<212> TYPE: DNA
<213> ORGANISM: Artificial
<220> FEATURE:
<223> OTHER INFORMATION: antisense strand of CTGF lasiRNA No.13

<400> SEQUENCE: 78
aaugucucuc acucucuggc uucaugccau g                                    31

<210> SEQ ID NO 79
<211> LENGTH: 21
```

```
<212> TYPE: DNA
<213> ORGANISM: Artificial
<220> FEATURE:
<223> OTHER INFORMATION: sense strand of CTGF siRNA No.14

<400> SEQUENCE: 79
gcgaagcuga ccuggaagat t                                            21

<210> SEQ ID NO 80
<211> LENGTH: 21
<212> TYPE: DNA
<213> ORGANISM: Artificial
<220> FEATURE:
<223> OTHER INFORMATION: antisense strand of CTGF siRNA No.14

<400> SEQUENCE: 80
ucuuccaggu cagcuucgct t                                            21

<210> SEQ ID NO 81
<211> LENGTH: 16
<212> TYPE: DNA
<213> ORGANISM: Artificial
<220> FEATURE:
<223> OTHER INFORMATION: sense strand of CTGF asiRNA No.14

<400> SEQUENCE: 81
aagcugaccu ggaaga                                                  16

<210> SEQ ID NO 82
<211> LENGTH: 21
<212> TYPE: DNA
<213> ORGANISM: Artificial
<220> FEATURE:
<223> OTHER INFORMATION: antisense strand of CTGF asiRNA No.14

<400> SEQUENCE: 82
ucuuccaggu cagcuucgct t                                            21

<210> SEQ ID NO 83
<211> LENGTH: 16
<212> TYPE: DNA
<213> ORGANISM: Artificial
<220> FEATURE:
<223> OTHER INFORMATION: sense strand of CTGF lasiRNA No.14

<400> SEQUENCE: 83
aagcugaccu ggaaga                                                  16

<210> SEQ ID NO 84
<211> LENGTH: 31
<212> TYPE: DNA
<213> ORGANISM: Artificial
<220> FEATURE:
<223> OTHER INFORMATION: antisense strand of CTGF lasiRNA No.14

<400> SEQUENCE: 84
ucuuccaggu cagcuucgca aggccugacc a                                 31

<210> SEQ ID NO 85
<211> LENGTH: 21
<212> TYPE: DNA
<213> ORGANISM: Artificial
<220> FEATURE:
<223> OTHER INFORMATION: sense strand of CTGF siRNA No.15

<400> SEQUENCE: 85
```
ccggagacaa ugacaucuut t         21

<210> SEQ ID NO 86
<211> LENGTH: 21
<212> TYPE: DNA
<213> ORGANISM: Artificial
<220> FEATURE:
<223> OTHER INFORMATION: antisense strand of CTGF siRNA No.15

<400> SEQUENCE: 86
aagaugucau ugucuccggt t         21

<210> SEQ ID NO 87
<211> LENGTH: 16
<212> TYPE: DNA
<213> ORGANISM: Artificial
<220> FEATURE:
<223> OTHER INFORMATION: sense strand of CTGF asiRNA No.15

<400> SEQUENCE: 87
gagacaauga caucuu               16

<210> SEQ ID NO 88
<211> LENGTH: 21
<212> TYPE: DNA
<213> ORGANISM: Artificial
<220> FEATURE:
<223> OTHER INFORMATION: antisense strand of CTGF asiRNA No.15

<400> SEQUENCE: 88
aagaugucau ugucuccggt t         21

<210> SEQ ID NO 89
<211> LENGTH: 16
<212> TYPE: DNA
<213> ORGANISM: Artificial
<220> FEATURE:
<223> OTHER INFORMATION: sense strand of CTGF lasiRNA No.15

<400> SEQUENCE: 89
gagacaauga caucuu               16

<210> SEQ ID NO 90
<211> LENGTH: 31
<212> TYPE: DNA
<213> ORGANISM: Artificial
<220> FEATURE:
<223> OTHER INFORMATION: antisense strand of CTGF lasiRNA No.15

<400> SEQUENCE: 90
aagaugucau ugucuccggg acaguuguaa u         31

<210> SEQ ID NO 91
<211> LENGTH: 21
<212> TYPE: DNA
<213> ORGANISM: Artificial
<220> FEATURE:
<223> OTHER INFORMATION: sense strand of CTGF siRNA No.16

<400> SEQUENCE: 91
ucuuugaauc gcuguacuat t         21

<210> SEQ ID NO 92
<211> LENGTH: 21
<212> TYPE: DNA
<213> ORGANISM: Artificial

```
<220> FEATURE:
<223> OTHER INFORMATION: antisense strand of CTGF siRNA No.16

<400> SEQUENCE: 92
uaguacagcg auucaaagat t                                              21

<210> SEQ ID NO 93
<211> LENGTH: 16
<212> TYPE: DNA
<213> ORGANISM: Artificial
<220> FEATURE:
<223> OTHER INFORMATION: sense strand of CTGF asiRNA No.16

<400> SEQUENCE: 93
uugaaucgcu guacua                                                    16

<210> SEQ ID NO 94
<211> LENGTH: 21
<212> TYPE: DNA
<213> ORGANISM: Artificial
<220> FEATURE:
<223> OTHER INFORMATION: antisense strand of CTGF asiRNA No.16

<400> SEQUENCE: 94
uaguacagcg auucaaagat t                                              21

<210> SEQ ID NO 95
<211> LENGTH: 16
<212> TYPE: DNA
<213> ORGANISM: Artificial
<220> FEATURE:
<223> OTHER INFORMATION: sense strand of CTGF lasiRNA No.16

<400> SEQUENCE: 95
uugaaucgcu guacua                                                    16

<210> SEQ ID NO 96
<211> LENGTH: 31
<212> TYPE: DNA
<213> ORGANISM: Artificial
<220> FEATURE:
<223> OTHER INFORMATION: antisense strand of CTGF lasiRNA No.16

<400> SEQUENCE: 96
uaguacagcg auucaaagau gcauugucu c                                    31

<210> SEQ ID NO 97
<211> LENGTH: 21
<212> TYPE: DNA
<213> ORGANISM: Artificial
<220> FEATURE:
<223> OTHER INFORMATION: sense strand of CTGF siRNA No.17

<400> SEQUENCE: 97
uugcgaagcu gaccuggaat t                                              21

<210> SEQ ID NO 98
<211> LENGTH: 21
<212> TYPE: DNA
<213> ORGANISM: Artificial
<220> FEATURE:
<223> OTHER INFORMATION: antisense strand of CTGF siRNA No.17

<400> SEQUENCE: 98
uuccagguca gcuucgcaat t                                              21
```

```
<210> SEQ ID NO 99
<211> LENGTH: 16
<212> TYPE: DNA
<213> ORGANISM: Artificial
<220> FEATURE:
<223> OTHER INFORMATION: sense strand of CTGF asiRNA No.17

<400> SEQUENCE: 99
cgaagcugac cuggaa                                                     16

<210> SEQ ID NO 100
<211> LENGTH: 21
<212> TYPE: DNA
<213> ORGANISM: Artificial
<220> FEATURE:
<223> OTHER INFORMATION: antisense strand of CTGF asiRNA No.17

<400> SEQUENCE: 100
uuccagguca gcuucgcaat t                                               21

<210> SEQ ID NO 101
<211> LENGTH: 16
<212> TYPE: DNA
<213> ORGANISM: Artificial
<220> FEATURE:
<223> OTHER INFORMATION: sense strand of CTGF lasiRNA No.17

<400> SEQUENCE: 101
cgaagcugac cuggaa                                                     16

<210> SEQ ID NO 102
<211> LENGTH: 31
<212> TYPE: DNA
<213> ORGANISM: Artificial
<220> FEATURE:
<223> OTHER INFORMATION: antisense strand of CTGF lasiRNA No.17

<400> SEQUENCE: 102
uuccagguca gcuucgcaag gccugaccau g                                    31

<210> SEQ ID NO 103
<211> LENGTH: 21
<212> TYPE: DNA
<213> ORGANISM: Artificial
<220> FEATURE:
<223> OTHER INFORMATION: sense strand of CTGF siRNA No.18

<400> SEQUENCE: 103
caacuaugau uagagccaat t                                               21

<210> SEQ ID NO 104
<211> LENGTH: 21
<212> TYPE: DNA
<213> ORGANISM: Artificial
<220> FEATURE:
<223> OTHER INFORMATION: antisense strand of CTGF siRNA No.18

<400> SEQUENCE: 104
uuggcucuaa ucauaguugt t                                               21

<210> SEQ ID NO 105
<211> LENGTH: 16
<212> TYPE: DNA
<213> ORGANISM: Artificial
<220> FEATURE:
<223> OTHER INFORMATION: sense strand of CTGF asiRNA No.18
```

<400> SEQUENCE: 105
cuaugauuag agccaa                                                    16

<210> SEQ ID NO 106
<211> LENGTH: 21
<212> TYPE: DNA
<213> ORGANISM: Artificial
<220> FEATURE:
<223> OTHER INFORMATION: antisense strand of CTGF asiRNA No.18

<400> SEQUENCE: 106
uuggcucuaa ucauaguugt t                                              21

<210> SEQ ID NO 107
<211> LENGTH: 16
<212> TYPE: DNA
<213> ORGANISM: Artificial
<220> FEATURE:
<223> OTHER INFORMATION: sense strand of CTGF lasiRNA No.18

<400> SEQUENCE: 107
cuaugauuag agccaa                                                    16

<210> SEQ ID NO 108
<211> LENGTH: 31
<212> TYPE: DNA
<213> ORGANISM: Artificial
<220> FEATURE:
<223> OTHER INFORMATION: antisense strand of CTGF lasiRNA No.18

<400> SEQUENCE: 108
uuggcucuaa ucauaguugg gucugggcca a                                   31

<210> SEQ ID NO 109
<211> LENGTH: 21
<212> TYPE: DNA
<213> ORGANISM: Artificial
<220> FEATURE:
<223> OTHER INFORMATION: sense strand of CTGF siRNA No.19

<400> SEQUENCE: 109
guaccagugc acgugccugt t                                              21

<210> SEQ ID NO 110
<211> LENGTH: 21
<212> TYPE: DNA
<213> ORGANISM: Artificial
<220> FEATURE:
<223> OTHER INFORMATION: antisense strand of CTGF siRNA No.19

<400> SEQUENCE: 110
caggcacgug cacugguact t                                              21

<210> SEQ ID NO 111
<211> LENGTH: 16
<212> TYPE: DNA
<213> ORGANISM: Artificial
<220> FEATURE:
<223> OTHER INFORMATION: sense strand of CTGF asiRNA No.19

<400> SEQUENCE: 111
ccagugcacg ugccug                                                    16

<210> SEQ ID NO 112

```
<211> LENGTH: 21
<212> TYPE: DNA
<213> ORGANISM: Artificial
<220> FEATURE:
<223> OTHER INFORMATION: antisense strand of CTGF asiRNA No.19

<400> SEQUENCE: 112
caggcacgug cacugguact t                                          21

<210> SEQ ID NO 113
<211> LENGTH: 16
<212> TYPE: DNA
<213> ORGANISM: Artificial
<220> FEATURE:
<223> OTHER INFORMATION: sense strand of CTGF lasiRNA No.19

<400> SEQUENCE: 113
ccagugcacg ugccug                                                16

<210> SEQ ID NO 114
<211> LENGTH: 31
<212> TYPE: DNA
<213> ORGANISM: Artificial
<220> FEATURE:
<223> OTHER INFORMATION: antisense strand of CTGF lasiRNA No.19

<400> SEQUENCE: 114
caggcacgug cacugguacu ugcagcugcu c                               31

<210> SEQ ID NO 115
<211> LENGTH: 21
<212> TYPE: DNA
<213> ORGANISM: Artificial
<220> FEATURE:
<223> OTHER INFORMATION: sense strand of CTGF siRNA No.20

<400> SEQUENCE: 115
agugcauccg uacucccaat t                                          21

<210> SEQ ID NO 116
<211> LENGTH: 21
<212> TYPE: DNA
<213> ORGANISM: Artificial
<220> FEATURE:
<223> OTHER INFORMATION: antisense strand of CTGF siRNA No.20

<400> SEQUENCE: 116
uugggaguac ggaugcacut t                                          21

<210> SEQ ID NO 117
<211> LENGTH: 16
<212> TYPE: DNA
<213> ORGANISM: Artificial
<220> FEATURE:
<223> OTHER INFORMATION: sense strand of CTGF asiRNA No.20

<400> SEQUENCE: 117
gcauccguac ucccaa                                                16

<210> SEQ ID NO 118
<211> LENGTH: 21
<212> TYPE: DNA
<213> ORGANISM: Artificial
<220> FEATURE:
<223> OTHER INFORMATION: antisense strand of CTGF asiRNA No.20

<400> SEQUENCE: 118
```

```
uugggaguac ggaugcacut t                                              21

<210> SEQ ID NO 119
<211> LENGTH: 16
<212> TYPE: DNA
<213> ORGANISM: Artificial
<220> FEATURE:
<223> OTHER INFORMATION: sense strand of CTGF lasiRNA No.20

<400> SEQUENCE: 119
gcauccguac ucccaa                                                    16

<210> SEQ ID NO 120
<211> LENGTH: 31
<212> TYPE: DNA
<213> ORGANISM: Artificial
<220> FEATURE:
<223> OTHER INFORMATION: antisense strand of CTGF lasiRNA No.20

<400> SEQUENCE: 120
uugggaguac ggaugcacuu uuugcccuuc u                                   31

<210> SEQ ID NO 121
<211> LENGTH: 21
<212> TYPE: DNA
<213> ORGANISM: Artificial
<220> FEATURE:
<223> OTHER INFORMATION: sense strand of CTGF siRNA No.21

<400> SEQUENCE: 121
caugauguuc aucaagacct t                                              21

<210> SEQ ID NO 122
<211> LENGTH: 21
<212> TYPE: DNA
<213> ORGANISM: Artificial
<220> FEATURE:
<223> OTHER INFORMATION: antisense strand of CTGF siRNA No.21

<400> SEQUENCE: 122
ggucuugaug aacaucaugt t                                              21

<210> SEQ ID NO 123
<211> LENGTH: 16
<212> TYPE: DNA
<213> ORGANISM: Artificial
<220> FEATURE:
<223> OTHER INFORMATION: sense strand of CTGF asiRNA No.21

<400> SEQUENCE: 123
gauguucauc aagacc                                                    16

<210> SEQ ID NO 124
<211> LENGTH: 21
<212> TYPE: DNA
<213> ORGANISM: Artificial
<220> FEATURE:
<223> OTHER INFORMATION: antisense strand of CTGF asiRNA No.21

<400> SEQUENCE: 124
ggucuugaug aacaucaugt t                                              21

<210> SEQ ID NO 125
<211> LENGTH: 16
<212> TYPE: DNA
```

-continued

<213> ORGANISM: Artificial
<220> FEATURE:
<223> OTHER INFORMATION: sense strand of CTGF lasiRNA No.21

<400> SEQUENCE: 125
gauguucauc aagacc                                               16

<210> SEQ ID NO 126
<211> LENGTH: 31
<212> TYPE: DNA
<213> ORGANISM: Artificial
<220> FEATURE:
<223> OTHER INFORMATION: antisense strand of CTGF lasiRNA No.21

<400> SEQUENCE: 126
ggucuugaug aacaucaugu ucuucuucau g                              31

<210> SEQ ID NO 127
<211> LENGTH: 21
<212> TYPE: DNA
<213> ORGANISM: Artificial
<220> FEATURE:
<223> OTHER INFORMATION: sense strand of CTGF siRNA No.22

<400> SEQUENCE: 127
ccaugaccgc cgccaguaut t                                         21

<210> SEQ ID NO 128
<211> LENGTH: 21
<212> TYPE: DNA
<213> ORGANISM: Artificial
<220> FEATURE:
<223> OTHER INFORMATION: antisense strand of CTGF siRNA No.22

<400> SEQUENCE: 128
auacuggcgg cggucauggt t                                         21

<210> SEQ ID NO 129
<211> LENGTH: 16
<212> TYPE: DNA
<213> ORGANISM: Artificial
<220> FEATURE:
<223> OTHER INFORMATION: sense strand of CTGF asiRNA No.22

<400> SEQUENCE: 129
ugaccgccgc caguau                                               16

<210> SEQ ID NO 130
<211> LENGTH: 21
<212> TYPE: DNA
<213> ORGANISM: Artificial
<220> FEATURE:
<223> OTHER INFORMATION: antisense strand of CTGF asiRNA No.22

<400> SEQUENCE: 130
auacuggcgg cggucauggt t                                         21

<210> SEQ ID NO 131
<211> LENGTH: 16
<212> TYPE: DNA
<213> ORGANISM: Artificial
<220> FEATURE:
<223> OTHER INFORMATION: sense strand of CTGF lasiRNA No.22

<400> SEQUENCE: 131
ugaccgccgc caguau                                               16

<210> SEQ ID NO 132
<211> LENGTH: 31
<212> TYPE: DNA
<213> ORGANISM: Artificial
<220> FEATURE:
<223> OTHER INFORMATION: antisense strand of CTGF lasiRNA No.22

<400> SEQUENCE: 132
auacuggcgg cggucauggu uggcacugcg g                          31

<210> SEQ ID NO 133
<211> LENGTH: 21
<212> TYPE: DNA
<213> ORGANISM: Artificial
<220> FEATURE:
<223> OTHER INFORMATION: sense strand of CTGF siRNA No.23

<400> SEQUENCE: 133
gaacauuaag aagggcaaat t                                     21

<210> SEQ ID NO 134
<211> LENGTH: 21
<212> TYPE: DNA
<213> ORGANISM: Artificial
<220> FEATURE:
<223> OTHER INFORMATION: antisense strand of CTGF siRNA No.23

<400> SEQUENCE: 134
uuugcccuuc uuaauguuct t                                     21

<210> SEQ ID NO 135
<211> LENGTH: 16
<212> TYPE: DNA
<213> ORGANISM: Artificial
<220> FEATURE:
<223> OTHER INFORMATION: sense strand of CTGF asiRNA No.23

<400> SEQUENCE: 135
cauuaagaag ggcaaa                                           16

<210> SEQ ID NO 136
<211> LENGTH: 21
<212> TYPE: DNA
<213> ORGANISM: Artificial
<220> FEATURE:
<223> OTHER INFORMATION: antisense strand of CTGF asiRNA No.23

<400> SEQUENCE: 136
uuugcccuuc uuaauguuct t                                     21

<210> SEQ ID NO 137
<211> LENGTH: 16
<212> TYPE: DNA
<213> ORGANISM: Artificial
<220> FEATURE:
<223> OTHER INFORMATION: sense strand of CTGF lasiRNA No.23

<400> SEQUENCE: 137
cauuaagaag ggcaaa                                           16

<210> SEQ ID NO 138
<211> LENGTH: 31
<212> TYPE: DNA
<213> ORGANISM: Artificial
<220> FEATURE:

<223> OTHER INFORMATION: antisense strand of CTGF lasiRNA No.23

<400> SEQUENCE: 138
uuugcccuuc uuaauguucu cuuccagguc a                            31

<210> SEQ ID NO 139
<211> LENGTH: 21
<212> TYPE: DNA
<213> ORGANISM: Artificial
<220> FEATURE:
<223> OTHER INFORMATION: sense strand of CTGF siRNA No.24

<400> SEQUENCE: 139
ggaagacacg uuuggcccat t                                       21

<210> SEQ ID NO 140
<211> LENGTH: 21
<212> TYPE: DNA
<213> ORGANISM: Artificial
<220> FEATURE:
<223> OTHER INFORMATION: antisense strand of CTGF siRNA No.24

<400> SEQUENCE: 140
ugggccaaac gugucuucct t                                       21

<210> SEQ ID NO 141
<211> LENGTH: 16
<212> TYPE: DNA
<213> ORGANISM: Artificial
<220> FEATURE:
<223> OTHER INFORMATION: sense strand of CTGF asiRNA No.24

<400> SEQUENCE: 141
agacacguuu ggccca                                             16

<210> SEQ ID NO 142
<211> LENGTH: 21
<212> TYPE: DNA
<213> ORGANISM: Artificial
<220> FEATURE:
<223> OTHER INFORMATION: antisense strand of CTGF asiRNA No.24

<400> SEQUENCE: 142
ugggccaaac gugucuucct t                                       21

<210> SEQ ID NO 143
<211> LENGTH: 16
<212> TYPE: DNA
<213> ORGANISM: Artificial
<220> FEATURE:
<223> OTHER INFORMATION: sense strand of CTGF lasiRNA No.24

<400> SEQUENCE: 143
agacacguuu ggccca                                             16

<210> SEQ ID NO 144
<211> LENGTH: 31
<212> TYPE: DNA
<213> ORGANISM: Artificial
<220> FEATURE:
<223> OTHER INFORMATION: antisense strand of CTGF lasiRNA No.24

<400> SEQUENCE: 144
ugggccaaac gugucuucca gucgguaagc c                            31

```
<210> SEQ ID NO 145
<211> LENGTH: 20
<212> TYPE: DNA
<213> ORGANISM: Artificial
<220> FEATURE:
<223> OTHER INFORMATION: forward primer

<400> SEQUENCE: 145
gagtcaacgg atttggtcgt                                                   20

<210> SEQ ID NO 146
<211> LENGTH: 20
<212> TYPE: DNA
<213> ORGANISM: Artificial
<220> FEATURE:
<223> OTHER INFORMATION: reverse primer

<400> SEQUENCE: 146
gacaagcttc ccgttctcag                                                   20

<210> SEQ ID NO 147
<211> LENGTH: 20
<212> TYPE: DNA
<213> ORGANISM: Artificial
<220> FEATURE:
<223> OTHER INFORMATION: CTGF forward primer

<400> SEQUENCE: 147
caagggcctc ttctgtgact                                                   20

<210> SEQ ID NO 148
<211> LENGTH: 20
<212> TYPE: DNA
<213> ORGANISM: Artificial
<220> FEATURE:
<223> OTHER INFORMATION: CTGF reverse primer

<400> SEQUENCE: 148
gacaagcttc ccgttctcag                                                   20

<210> SEQ ID NO 149
<211> LENGTH: 21
<212> TYPE: DNA
<213> ORGANISM: Artificial
<220> FEATURE:
<223> OTHER INFORMATION: sense strand of siRNA

<400> SEQUENCE: 149
cggcuuaccg acuggaagat t                                                 21

<210> SEQ ID NO 150
<211> LENGTH: 21
<212> TYPE: DNA
<213> ORGANISM: Artificial
<220> FEATURE:
<223> OTHER INFORMATION: antisense strand of siRNA

<400> SEQUENCE: 150
ucuuccaguc gguaagccgt t                                                 21

<210> SEQ ID NO 151
<211> LENGTH: 16
<212> TYPE: DNA
<213> ORGANISM: Artificial
<220> FEATURE:
<223> OTHER INFORMATION: sense strand of asiRNA
```

-continued

```
<400> SEQUENCE: 151
cuuaccgacu ggaaga                                                       16

<210> SEQ ID NO 152
<211> LENGTH: 21
<212> TYPE: DNA
<213> ORGANISM: Artificial
<220> FEATURE:
<223> OTHER INFORMATION: antisense strand of asiRNA

<400> SEQUENCE: 152
ucuuccaguc gguaagccgt t                                                 21

<210> SEQ ID NO 153
<211> LENGTH: 16
<212> TYPE: DNA
<213> ORGANISM: Artificial
<220> FEATURE:
<223> OTHER INFORMATION: sense strand of lasiRNA

<400> SEQUENCE: 153
cuuaccgacu ggaaga                                                       16

<210> SEQ ID NO 154
<211> LENGTH: 31
<212> TYPE: DNA
<213> ORGANISM: Artificial
<220> FEATURE:
<223> OTHER INFORMATION: antisense strand of lasiRNA

<400> SEQUENCE: 154
ucuuccaguc gguaagccgc gagggcaggc c                                      31

<210> SEQ ID NO 155
<211> LENGTH: 16
<212> TYPE: DNA
<213> ORGANISM: Artificial
<220> FEATURE:
<223> OTHER INFORMATION: sense strand of Chol-lasiRNA-PS(0)

<400> SEQUENCE: 155
cuuaccgacu ggaaga                                                       16

<210> SEQ ID NO 156
<211> LENGTH: 31
<212> TYPE: DNA
<213> ORGANISM: Artificial
<220> FEATURE:
<223> OTHER INFORMATION: antisense strand of Chol-lasiRNA-PS(0)

<400> SEQUENCE: 156
ucuuccaguc gguaagccgc gagggcaggc c                                      31

<210> SEQ ID NO 157
<211> LENGTH: 16
<212> TYPE: DNA
<213> ORGANISM: Artificial
<220> FEATURE:
<223> OTHER INFORMATION: sense strand of Chol-lasiRNA-PS(4)

<400> SEQUENCE: 157
cuuaccgacu ggaaga                                                       16

<210> SEQ ID NO 158
<211> LENGTH: 31
```

-continued

```
<212> TYPE: DNA
<213> ORGANISM: Artificial
<220> FEATURE:
<223> OTHER INFORMATION: antisense strand of Chol-lasiRNA-PS(4)

<400> SEQUENCE: 158
ucuuccaguc gguaagccgc gagggcaggc c                                    31

<210> SEQ ID NO 159
<211> LENGTH: 16
<212> TYPE: DNA
<213> ORGANISM: Artificial
<220> FEATURE:
<223> OTHER INFORMATION: sense strand of Chol-lasiRNA-PS(7)

<400> SEQUENCE: 159
cuuaccgacu ggaaga                                                     16

<210> SEQ ID NO 160
<211> LENGTH: 31
<212> TYPE: DNA
<213> ORGANISM: Artificial
<220> FEATURE:
<223> OTHER INFORMATION: antisense strand of Chol-lasiRNA-PS(7)

<400> SEQUENCE: 160
ucuuccaguc gguaagccgc gagggcaggc c                                    31

<210> SEQ ID NO 161
<211> LENGTH: 16
<212> TYPE: DNA
<213> ORGANISM: Artificial
<220> FEATURE:
<223> OTHER INFORMATION: sense strand of Chol-lasiRNA-PS(12)

<400> SEQUENCE: 161
cuuaccgacu ggaaga                                                     16

<210> SEQ ID NO 162
<211> LENGTH: 31
<212> TYPE: DNA
<213> ORGANISM: Artificial
<220> FEATURE:
<223> OTHER INFORMATION: antisense strand of Chol-lasiRNA-PS(12)

<400> SEQUENCE: 162
ucuuccaguc gguaagccgc gagggcaggc c                                    31

<210> SEQ ID NO 163
<211> LENGTH: 16
<212> TYPE: DNA
<213> ORGANISM: Artificial
<220> FEATURE:
<223> OTHER INFORMATION: sense strand of Chol-lasiRNA-PS(17)

<400> SEQUENCE: 163
cuuaccgacu ggaaga                                                     16

<210> SEQ ID NO 164
<211> LENGTH: 31
<212> TYPE: DNA
<213> ORGANISM: Artificial
<220> FEATURE:
<223> OTHER INFORMATION: antisense strand of Chol-lasiRNA-PS(17)

<400> SEQUENCE: 164
```
ucuuccaguc gguaagccgc gagggcaggc c                                   31

<210> SEQ ID NO 165
<211> LENGTH: 16
<212> TYPE: DNA
<213> ORGANISM: Artificial
<220> FEATURE:
<223> OTHER INFORMATION: sense strand of Chol-lasiRNA-PS(7)-cy3

<400> SEQUENCE: 165
cuuaccgacu ggaaga                                                   16

<210> SEQ ID NO 166
<211> LENGTH: 31
<212> TYPE: DNA
<213> ORGANISM: Artificial
<220> FEATURE:
<223> OTHER INFORMATION: antisense strand of Chol-lasiRNA-PS(7)-cy3

<400> SEQUENCE: 166
ucuuccaguc gguaagccgc gagggcaggc c                                   31

<210> SEQ ID NO 167
<211> LENGTH: 16
<212> TYPE: DNA
<213> ORGANISM: Artificial
<220> FEATURE:
<223> OTHER INFORMATION: sense strand of Chol-lasiRNA-PS(7)

<400> SEQUENCE: 167
ccagaccaaa uuugca                                                   16

<210> SEQ ID NO 168
<211> LENGTH: 31
<212> TYPE: DNA
<213> ORGANISM: Artificial
<220> FEATURE:
<223> OTHER INFORMATION: antisense strand of Chol-lasiRNA-PS(7)

<400> SEQUENCE: 168
ugcaaauuug gucuggaagu cacauuccuu g                                   31

<210> SEQ ID NO 169
<211> LENGTH: 31
<212> TYPE: DNA
<213> ORGANISM: Artificial
<220> FEATURE:
<223> OTHER INFORMATION: antisense strand of cp-lasiRNA (survivin)

<400> SEQUENCE: 169
ugaaaauguu gaucuccuuu ccuaagacat t                                   31

<210> SEQ ID NO 170
<211> LENGTH: 16
<212> TYPE: DNA
<213> ORGANISM: Artificial
<220> FEATURE:
<223> OTHER INFORMATION: sense strand of cp-lasiRNA (survivin)

<400> SEQUENCE: 170
gagaucaaca uuuuca                                                   16

<210> SEQ ID NO 171
<211> LENGTH: 21
<212> TYPE: DNA
<213> ORGANISM: Artificial

```
<220> FEATURE:
<223> OTHER INFORMATION: antisense strand of cp-lasiRNA (survivin)

<400> SEQUENCE: 171
ugaaaauguu gaucuccuuu c                                              21

<210> SEQ ID NO 172
<211> LENGTH: 20
<212> TYPE: DNA
<213> ORGANISM: Artificial
<220> FEATURE:
<223> OTHER INFORMATION: primer

<400> SEQUENCE: 172
gcaccacttc cagggtttat                                                20

<210> SEQ ID NO 173
<211> LENGTH: 20
<212> TYPE: DNA
<213> ORGANISM: Artificial
<220> FEATURE:
<223> OTHER INFORMATION: primer

<400> SEQUENCE: 173
ctctggtgcc actttcaaga                                                20

<210> SEQ ID NO 174
<211> LENGTH: 31
<212> TYPE: DNA
<213> ORGANISM: Artificial
<220> FEATURE:
<223> OTHER INFORMATION: cp-lasiRNA (CTGF) antisense 31nt

<400> SEQUENCE: 174
ucuuccaguc gguaagccgc gagggcaggc c                                   31

<210> SEQ ID NO 175
<211> LENGTH: 16
<212> TYPE: DNA
<213> ORGANISM: Artificial
<220> FEATURE:
<223> OTHER INFORMATION: cp-lasiRNA (CTGF) sense

<400> SEQUENCE: 175
cttaccgact ggaaga                                                    16

<210> SEQ ID NO 176
<211> LENGTH: 21
<212> TYPE: DNA
<213> ORGANISM: Artificial
<220> FEATURE:
<223> OTHER INFORMATION: cp-lasiRNA (CTGF) antisense 21nt

<400> SEQUENCE: 176
ucuuccaguc gguaagccgc g                                              21

<210> SEQ ID NO 177
<211> LENGTH: 31
<212> TYPE: DNA
<213> ORGANISM: Artificial
<220> FEATURE:
<223> OTHER INFORMATION: cp-lasiRNA (CTGF) Antisense Rat
```

<400> SEQUENCE: 177
ucuuccaguc gguaggcagc uagggcaggg c					31

<210> SEQ ID NO 178
<211> LENGTH: 16
<212> TYPE: DNA
<213> ORGANISM: Artificial
<220> FEATURE:
<223> OTHER INFORMATION: cp-lasiRNA (CTGF) Sense Rat

<400> SEQUENCE: 178
cctaccgact ggaaga					16

<210> SEQ ID NO 179
<211> LENGTH: 21
<212> TYPE: DNA
<213> ORGANISM: Artificial
<220> FEATURE:
<223> OTHER INFORMATION: siRNA (CTGF) antisense

<400> SEQUENCE: 179
cugccuaccg acuggaagat t					21

<210> SEQ ID NO 180
<211> LENGTH: 21
<212> TYPE: DNA
<213> ORGANISM: Artificial
<220> FEATURE:
<223> OTHER INFORMATION: siRNA (CTGF) sense

<400> SEQUENCE: 180
cugccuaccg acuggaagat t					21

<210> SEQ ID NO 181
<211> LENGTH: 17
<212> TYPE: DNA
<213> ORGANISM: Artificial
<220> FEATURE:
<223> OTHER INFORMATION: primer

<400> SEQUENCE: 181
ggctcgcatc atagttg					17

<210> SEQ ID NO 182
<211> LENGTH: 20
<212> TYPE: DNA
<213> ORGANISM: Artificial
<220> FEATURE:
<223> OTHER INFORMATION: primer

<400> SEQUENCE: 182
cgggaaatgc tgtgaggagt					20

RNA-INTERFERENCE-INDUCING NUCLEIC ACID MOLECULE ABLE TO PENETRATE INTO CELLS, AND USE THEREFOR

CROSS-REFERENCE TO RELATED APPLICATIONS

This application is a U.S. national phase under the provisions of 35 U.S.C. § 371 of International Patent Application No. PCT/KR13/04463 filed May 21, 2013, which in turn claims priority of Korean Patent Application No. 10-2012-0053950 filed May 22, 2012. The disclosures of such international patent application and Korean priority patent application are hereby incorporated herein by reference in their respective entireties, for all purposes.

TECHNICAL FIELD

The present invention relates to a novel, RNA interference (RNAi)-inducing nucleic acid molecule having cell penetrating ability and the use thereof, and more particularly, to a novel, RNAi-inducing double-stranded nucleic acid molecule, which has a replacement of the phosphate backbone of at least one nucleotide with phosphorothioate or phosphorodithioate, and has a lipophilic compound conjugated thereto, and thus has high target gene-silencing efficiency while having the ability to penetrate cells without needing a separate intracellular delivery vehicle, and to a method of silencing a target gene using the nucleic acid molecule.

BACKGROUND ART

RNA interference (RNAi) is a mechanism capable of inhibiting the expression of a gene in a highly specific and efficient manner, in which degradation of the mRNA of a target gene is induced by introducing a double-stranded RNA, which comprises a sense strand having a sequence homologous to the mRNA of the target gene and an antisense strand having a sequence complementary to the mRNA of the target gene, into cells or the like, thereby inhibiting the expression of the target gene.

An siRNA that induces this RNA interference is a short (19-21 bp) double-stranded RNA capable of inhibiting the expression of a target gene in a sequence-specific manner, and is currently receiving attention as a therapeutic agent against various diseases, including cancer difficult to treat, viral infections, and hereditary diseases, thanks to its high efficiency and target specificity. For the development of effective therapeutic agents based on an siRNA, various problems associated with stability, silencing efficiency, immune responses, off-target effects and the like, are required to be solved, and among them, effective in vivo delivery is considered most difficult to achieve. An siRNA cannot pass through the cell membrane, because it is highly negatively charged due to its phosphate backbone structure. In addition, because of its small size, the siRNA is quickly removed from blood, and thus it is difficult to deliver the siRNA in an amount sufficient for inducing RNAi to a target area.

In the case of in vitro delivery, many high-efficiency delivery methods that use cationic lipids and cationic polymers have been developed (Sioud M, Sorensen D R Cationic liposome-mediated delivery of siRNAs in adult mice. Biochem Biophys Res Commun 2003; 312: 1220-1225). However, in most cases, in vivo delivery of siRNAs is difficult to achieve with high efficiency, unlike in vitro delivery, and the efficiency of delivery of siRNAs decreases due to their interactions with various proteins in vivo (Bolcato-Bellemin A L, Bonnet M E, Creusat G, et al. Sticky overhangs enhance siRNA-mediated gene silencing. Proceedings of the National Academy of Sciences of the United States of America 2007; 104: 16050-16055). In addition, siRNAs are highly accumulated in a specific organ such as liver or lung, which is not a diseased area, depending on the composition of delivery vehicles, thus inducing toxicity.

Meanwhile, connective tissue growth factor (CTGF/CCN2) is known as a matricellular protein that plays an important role in the differentiation, growth, migration, ECM production, adhesion and the like of cells. In the case of chronic fibrotic disorders that induce fibrosis in various organs to cause damage to the organs, it was found that CTGF is overexpressed in tissues in which fibrotic disorders occur. Also, the relationship between CTGF and fibrosis in the skin has been relatively well studied. In addition, it was observed that the expression of CTGF in a normal skin was inhibited to the basal level, but temporarily increased when the skin was wounded. On the contrary, in the case of keloid or localized sclerosis, it was observed that the overexpression of CTFG was maintained even after wound healing, and when the expression of CTGF was inhibited using an antisense strand or the like, fibrosis and keloid production were inhibited, suggesting that CTGF plays an important role in fibrosis and keloid production (Sisco M, Kryger Z B, O'Shaughnessy K D, et al. Antisense inhibition of connective tissue growth factor (CTGF/CCN2) mRNA limits hypertrophic scarring without affecting wound healing in vivo. Wound Repair Regen 2008; 16: 661-673. DOI: WRR416 [pii]). Pathologically, it is known that a full-length CTGF molecule is involved in a condition in which the hyperproliferation of connective tissue cells and the excessive deposition of extracellular matrix are present. In addition, it is known that CTGF is also involved in conditions associated with the migration and proliferation of endothelial cells and angiogenesis. Examples of diseases and disorders associated with such conditions include the fibrosis, cancer and related diseases and disorders of the skin and major organs, for example, systemic sclerosis, angiogenesis, atherosclerosis, diabetic nephropathy, and renal hypertension. Also, CTGF is known to be useful for wound healing, connective tissue repair, and bone and cartilage repair. In such terms, CTGF was disclosed as an inducer of bone, tissue or cartilage formation disorders such as osteoporosis, osteoarthritis or osteochondritis, arthritis, skeletal disorder, hypertrophic scar, a burn, hemagiectatic hypertrophy, or sound healing (see, for example, U.S. Pat. No. 5,837,258).

Accordingly, the present inventors have made extensive efforts to provide a novel, RNAi-inducing nucleic acid molecule that can be effectively delivered in vitro and in vivo and has cell-penetrating ability, and as a result, have found that, when the phosphate backbone of at least one nucleotide in an RNAi-inducing double-stranded nucleic acid molecule is substituted with phosphorothioate and a lipophilic compound is conjugated to the nucleic acid molecule, the nucleic acid molecule exhibits high target gene silencing efficiency even in vivo without needing a separate intracellular delivery vehicle and, at the same time, has high cell-penetrating ability, thereby completing the present invention.

The above information disclosed in this Background section is only for enhancement of understanding of the background of the present invention, and therefore it may contain information that does not form the prior art that is already known to a person of ordinary skill in the art.

PRIOR ART LITERATURE

Patent Documents

Patent Document 1: U.S. Pat. No. 5,837,258

Non-Patent Documents

Non-Patent Document 1: Sioud M, Sorensen D R Cationic liposome-mediated delivery of siRNAs in adult mice. Biochem Biophys Res Commun 2003; 312: 1220-1225

Non-Patent Document 2: Bolcato-Bellemin A L, Bonnet M E, Creusat G, et al. Sticky overhangs enhance siRNA-mediated gene silencing. Proceedings of the National Academy of Sciences of the United States of America 2007; 104: 16050-16055

Non-Patent Document 3: Sisco M, Kryger Z B, O'Shaughnessy K D, et al. Antisense inhibition of connective tissue growth factor (CTGF/CCN2) mRNA limits hypertrophic scarring without affecting wound healing in vivo. Wound Repair Regen 2008; 16: 661-673. DOI: WRR416 [pii]

SUMMARY

It is an object of the present invention to provide a novel, RNAi-inducing nucleic acid molecule having cell-penetrating ability, which can be effectively delivered in vitro and in vivo, and the use thereof.

To achieve the above object, the present invention provides an RNAi-inducing double-stranded nucleic acid molecule having cell-penetrating ability, wherein the nucleic acid molecule comprising a first strand comprising a region complementary to a target nucleic acid and a second strand that forms a complementary bond with the first strand; and wherein the phosphate backbone of at least one nucleotide in the nucleic acid molecule was substituted with phosphorothioate or phosphorodithioate, and the nucleic acid molecule has a lipophilic compound conjugated thereto.

The present invention also provides a gene-silencing composition containing the above nucleic acid molecule.

The present invention also provides a method for silencing a target gene in a cell, the method comprising introducing the above nucleic acid molecule into the cell.

The present invention also provides a pharmaceutical composition for treating or preventing a connective tissue growth factor (CTGF)-associated disease or disorder, the composition containing the above nucleic acid molecule that targets a CTGF-encoding mRNA.

The present invention also provides a method of treating or preventing a connective tissue growth factor (CTGF)-associated disease or disorder comprising administering a pharmaceutical composition containing the above nucleic acid molecule targeting a CTGF-encoding mRNA.

The present invention also provides an RNAi-inducing double-stranded nucleic acid molecule having cell-penetrating ability, the nucleic acid molecule comprising: a first strand comprising a region complementary to a connective tissue growth factor (CTGF)-encoding mRNA; and a second strand that forms a complementary bond with the first strand, wherein the phosphate backbone of 1 to 31 nucleotides in the nucleic acid molecule was substituted with phosphorothioate or phosphorodithioate, and the nucleic acid molecule has a lipophilic compound conjugated thereto and has a pair of nucleic sequences selected from the group consisting of a pair of nucleotide sequences of SEQ ID NOS: 149 and 150, a pair of nucleotide sequences of SEQ ID NOS: 151 and 152, and a pair of nucleotide sequences of SEQ ID NOS: 153 and 154.

Other features and embodiments of the present invention will be more apparent from the following detailed descriptions and the appended claims.

BRIEF DESCRIPTION OF THE DRAWINGS

FIG. 3 shows the structures of cholesterol- and PS-modified lasiRNAs according to the present invention. Underline: OMe modification; *: PS modification, Chol: cholesterol; Cy3: Cy3.

FIG. 6 shows the structure of a chol-lasiRNA-PS7 that targets MyD88. Underline: OMe modification, *: PS modification, and Chol: cholesterol.

DETAILED DESCRIPTION

Figure 1:
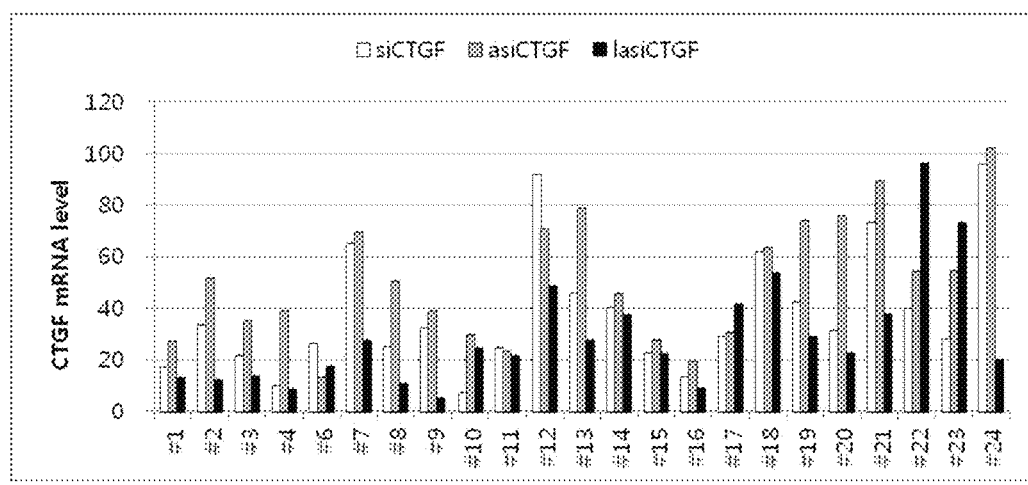
FIG. 1 is a graph showing the gene silencing efficiencies of siRNA, asiRNA and lasiRNA structures for 24 sequences that target the CTGFs shown in Tables 1 to 3.

Unless otherwise defined, all technical and scientific terms used herein have the same meaning as commonly understood by one of ordinary skill in the art to which the invention pertains. Generally, the nomenclature used herein are well known and commonly used in the art.

The definition of main terms used in the detailed description of the invention is as follows.

As used herein, the term "RNAi" (RNA interference) refers to a mechanism by which a double-stranded RNA (dsRNA) consisting of a strand having a sequence complementary to the mRNA of a target gene and a strand having a sequence complementary thereto is introduced into cells or the like to induce the degradation of the mRNA of the target gene to thereby inhibit the expression of the target gene.

As used herein, the term "siRNA" (small interfering RNA) refers to a short double-stranded RNA (dsRNA) that mediates efficient gene silencing in a sequence-specific manner.

As used herein, the term "antisense strand" refers to a polynucleotide that is substantially or 100% complementary to a target nucleic acid of interest. For example, an antisense strand may be complementary, in whole or in part, to a molecule of mRNA (messenger RNA), an RNA sequence that is not mRNA (e.g., microRNA, piwiRNA, tRNA, rRNA and hnRNA) or a sequence of DNA that is either coding or non-coding. The terms "antisense strand" and "guide strand" are used interchangeably herein.

The term "sense strand" refers to a polynucleotide that has the same nucleotide sequence, in whole or in part, as a target nucleic acid, in which the polynucleotide is identical, in whole or in part, a molecule of mRNA (messenger RNA), an RNA sequence that is not mRNA (e.g., microRNA, piwiRNA, tRNA, rRNA and hnRNA) or a sequence of DNA that is either coding or non-coding.

As used herein, the term "gene" is intended to have the broadest meaning, and the gene can encode a structural protein or a regulatory protein. Herein, the regulatory protein includes a transcriptional factor, a heat shock proteins, or a protein that is involved in DNA/RNA replication, transcription and/or translation. Also, the target gene whose expression is to be inhibited is resident in a viral genome which has integrated into the animal gene or may be present as an extrachromosomal element. For example, the target gene may be a gene on an HIV genome. In this case, the genetic construct is useful in inactivating translation of the HIV gene in a mammalian cell.

In one aspect, the present invention is directed to an RNAi-inducing double-stranded nucleic acid molecule having cell-penetrating ability, the nucleic acid molecule comprising a first strand comprising a region complementary to a target nucleic acid; and a second strand that forms a complementary bond with the first strand, wherein the phosphate backbone of at least one nucleotide in the nucleic acid molecule was substituted with phosphorothioate or phosphorodithioate, and the nucleic acid molecule has a lipophilic compound conjugated thereto.

Herein, the first strand corresponds to an antisense strand of siRNA, and the second strand corresponds to a sense strand of siRNA.

In the present invention, the first strand in the RNAi-inducing double-stranded nucleic acid molecule may have a length of 16 to 121 nt, and preferably 24-121 nt. The first strand comprises a region complementary to the target nucleic acid, and the region complementary to the target nucleic acid may have a length of 16 to 31 nt, 19 to 31 nt, or 19 to 21 nt. In addition, the second strand may have a length of 13 to 25 nt, 13 to 21 nt, or 16 to 21 nt.

In the present invention, preferably, the RNAi-inducing double-stranded nucleic acid molecule may comprise a first strand, which is 24-121 nt in length and comprises a region complementary to a target nucleic acid, and a second strand which is 13-21 nt in length and comprises a region that binds complementarily to the region of the first strand, which is complementary to the target nucleic acid.

In an example of the present invention, the nucleic acid molecule having the above-described structure was constructed to have each of 24 sequences targeting CTGF, and as a result, it was found that the constructed nucleic acid molecules generally had high gene silencing efficiencies compared to conventional siRNAs. In the present invention, an RNAi-inducing double-stranded nucleic acid molecule having a long single-stranded region that does not form a complementary bond with the second strand, that is, an siRNA having a long antisense strand, has been named as "lasiRNA".

The lasiRNA is a novel, asymmetrical RNAi-inducing structure that has a short double-strand length and high gene silencing efficiency, compared to conventional siRNA. In addition, due to the function of the antisense strand having a long overhang structure, the lasiRNA has increased gene silencing efficiency compared to siRNA or asiRNA, and thus will substitute for conventional structures to develop therapeutic agents. In addition, it is characterized in that in that it has a long overhang length compared to other structures, and maintains high activity even when the overhang is modified in various ways. By virtue of these characteristics, relatively many chemical modifications can be freely introduced into the lasiRNA, and thus various functions can be added to the lasiRNA.

In the present invention, the region of the first strand, which is complementary to the target nucleic acid, is preferably 19-21 nt in length. Thus, the first strand comprises a single-stranded region which does not bind to the second strand. Preferably, the first strand may further comprise, in the single-stranded region, a nucleic acid oligonucleotide selected from the group consisting of antisense DNA, antisense RNA, ribozyme and DNAzyme.

In the present invention, the single-stranded region of the first strand, which does not bind complementarily to the second strand, can be linked directly or by a linker to the region that binds complementarily to the second strand. Herein, the linker may be a chemical linker. Examples of the chemical linker include, but are not limited to, a nucleic acid moiety, PNA (a PNA moiety), a peptide moiety, a disulfide bond or a polyethylene glycol moiety.

Moreover, in the present invention, the first strand may further comprise, in the single-stranded region, a sequence that is complementary or non-complementary to the target nucleic acid. When the first strand comprises the complementary sequence, the complementary sequence may be located consecutively from the double-stranded region of the nucleic acid molecule of the present invention, that is, the region of siRNA, which is complementary to the target nucleic acid. Alternatively, the complementary sequence may also be located apart from the double-stranded region. Likewise, the sequence that is targeted by siRNA, and the sequence that is targeted by the ribozyme or DNAzyme of the single-stranded region may be located consecutively or located apart from each other. In addition, in the case in which the single-stranded region of the first strand has the sequence of siRNA, which is complementary to the target gene, when the sequence contained in the single-stranded region is antisense DNA or antisense RNA, the sequence may be at least about 70-80%, more preferably at least about 80-90%, and even more preferably at least 95-99% complementary to the sequence of the target gene targeted by the siRNA, and when the single-stranded region is ribozyme or DNAzyme, the sequence of the single-stranded region may be at least about 50-60% complementary to the sequence of the target gene targeted by the siRNA.

In addition, the single-stranded region may be 5-100 nt in length. If the length of the single-stranded region is less than 5 nt, the effect of increasing the efficiency with which gene expression is inhibited will be insignificant, and if the length is more than 100 nt, the efficiency with which an RNA molecule is synthesized will be reduced. Preferably, the single-stranded region may be 9-100 nt in length or 50 nt or less in length. More preferably, the single-stranded region may be 10-15 nt in length.

In the present invention, at least one of the nucleotides of the single-stranded region in the first strand may comprise a bulky base analog. When an extended sequence comprises a bulky base analog such as a deoxyadenosine derivative having a phenyl group, an mRNA strand that binds complementarily to the extended sequence is cleaved at the location of the bulky base analog. Any bulky base analog that induces this cleavage may be used without limitation in the present invention.

In the present invention, in case of a nucleic structure obtained by extending the antisense strand of siRNA in a manner complementary to a target mRNA sequence, it was predicted that the 5' end of the nucleic structure will function as the RNAi mechanism while the 3' end of the nucleic structure will function as an antisense mechanism or guide the 5' end siRNA to the target mRNA. When the sequence of the antisense 3'-end, which is complementary to mRNA, is DNA, it can induce RNase H-dependent mRNA cleavage. In addition, it was predicted that when at least one of the nucleotides of the single-stranded region of the antisense 3'-end comprises a bulky base analog or the single-stranded region binds to mRNA to form a bulge structure, cleavage could be induced. Further, when a nucleic acid molecule comprising the ribozyme or DNAzyme introduced into the single-stranded region of the first strand can induce synergistic cleavage.

Korean Patent Laid-Open Publication No. 10-2009-0065880 discloses an siRNA structure which is an siRNA molecule consisting of a 19-21 nt antisense strand and a 13-16 nt sense strand, in which the 5' end of the antisense strand is a blunt end. This siRNA structure inhibits gene expression at high efficiency without causing off-target effects by the sense strand of siRNA or inhibiting other RNAi mechanisms. When the structure of the present invention is applied to this siRNA, off-target effects can be minimized while the above-described effect of the nucleic acid oligonucleotide contained in the single-stranded region of the first strand can be obtained. As used herein, the term "off-target effects" refers to any instance in which the sense strand of siRNA causes the unexpected degradation of other mRNAs or the silencing of the corresponding genes, and the antisense strand of siRNA is paired with undesired targets to cause the degradation of other mRNAs or the silencing of the corresponding genes, even though siRNA is originally used to induce the degradation of mRNA having a sequence complementary to the antisense strand so as to obtain the effect of inhibiting the gene expression of the mRNA.

In an example of the present invention, it was shown that, when cholesterol modifications and PS modifications were performed, the cholesterol modifications increased the cell penetrating ability of the lasiRNA, but when a sufficient number of phosphorothioate (PS) modifications were not introduced, the use of cholesterol alone was not sufficient to effectively induce target gene silencing without a separate intracellular delivery system. Herein, it was shown that the introduction of PS modifications increased the cell penetrating ability in proportion to the number of PS modifications introduced, and when the number of PS modifications was too large, the lasiRNA did not induce RNAi-mediated gene silencing. For this reason, the optimum number of PS modifications was established by comparing gene silencing efficiency after incubation with cells. Specifically, the nucleic acid molecule according to the present invention may characterized in that the phosphate backbone of 1 to 48 nucleotides, preferably 1 to 31 nucleotides, more preferably 2 to 17 nucleotides, and even more preferably 4 to 17 or 12 to 17 nucleotides, is substituted with phosphorothioate.

Herein, the phosphate backbone of nucleotides in the first strand of the nucleic acid molecule may be substituted with phosphorothioate, and the phosphate backbones of nucleotides in a region of the first strand, which excludes a region complementary to a target nucleic acid, may be substituted with phosphorothioate. Herein, the phosphate backbone of 1 to 31 nucleotides, preferably 1 to 17 nucleotides, more preferably 2 to 17 nucleotides, and even more preferably 4 to 17 nucleotides or 12 to 17 nucleotides, in the first strand, may be substituted with phosphorothioate. In addition, the phosphate backbone of 1 to 21 nucleotides, preferably 1 to 17 nucleotides, more preferably 2 to 17 nucleotides, and even more preferably 4 to 17 nucleotides or to 17 nucleotides, in the second strand, may be substituted with phosphorothioate.

Figure 10:
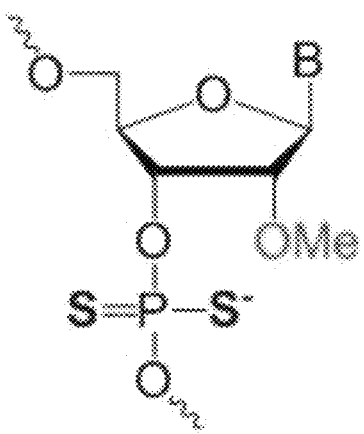
FIG. 10 shows the structure of a PS2 modification.

In another example of the present invention, it could be seen that the use of PS2 (phosphorodithioate) modification as shown in FIG. 10 in place of PS modification resulted in an increase in the gene silencing efficiency of the inventive nucleic acid molecule compared to conventional siRNA structures, even though it showed reduced gene silencing efficiency compared to PS modification. Thus, the nucleic acid molecule according to the present invention may be characterized in that the phosphate backbone of at least one nucleotide is substituted with phosphorodithioate. Preferably, the phosphate backbone of 1 to 48 nucleotides, preferably 1 to 31 nucleotides, more preferably 2 to 17 nucleotides, and even more preferably 4 to 17 or 12 to 17 nucleotides, in the nucleic acid molecule, may be substituted with phosphorodithioate. Herein, the phosphate backbone of 1 to 31 nucleotides, preferably 1 to 17 nucleotides, more preferably 2 to 17 nucleotides, and even more preferably 4 to or 12 to 17 nucleotides, in the first strand, may be substituted with phosphorodithioate. Alternatively, the phosphate backbone of 1 to 17 nucleotides, preferably 2 to 17 nucleotides, and even more preferably 4 to 17 or 12 to 17 nucleotides, in the second strand, may be substituted with phosphorodithioate.

The lipophilic compound that is used in the present invention results in hydrophobic modification, and may be, for example, a lipid, a lipophilic peptide or a lipophilic protein. As the lipid, cholesterol, tocopherol, or a long-chain fatty acid having 10 or more carbon atoms such as stearic acid or palmitic acid, may be used, but is not limited thereto. In addition, the lipophilic compound such as cholesterol may be conjugated to the 5' or 3' end of the first or second strand of the nucleic acid molecule, but is not limited thereto.

The target nucleic acid, not limited thereto, but might be mRNA (messenger RNA), microRNA, piRNA (piwi-interacting RNA), coding DNA sequence or non-coding DNA sequence or the like.

The nucleic acid molecule of the present invention may be a molecule synthesized according to a general method, but is not limited thereto. In other words, in the present invention, the siRNA molecule may be chemically or enzymatically synthesized. The siRNA molecule of the present invention may be derived from naturally occurring genes by standard recombinant techniques. In this case, the siRNA molecule may be substantially complementary at the nucleotide sequence level to at least a portion of mRNA of the target gene, the expression of which is to be modified.

Accordingly, the nucleic acid molecule of the present invention may comprise a chemical modification. The chemical modification may be obtained by replacing the hydroxyl group at position 2' of ribose of at least one nucleotide, included in the nucleic acid molecule, by any one of a hydrogen atom, a fluorine atom, an —O-alkyl group, an —O-acyl group and an amino group, but is not limited thereto. In order to increase the ability to deliver the nucleic acid molecule, the hydroxyl group may be substituted by any one of —Br, —Cl, —R, —R'OR, —SH, —SR, —N$_3$ and —CN (R=alkyl, aryl, or alkylene). In addition, the chemical modification may be obtained by replacing the phosphate backbone of at least one nucleotide, included in the nucleic acid molecule, by any one of alkylphosphonate form, phosphoroamidate form and boranophosphate form. Further, the chemical modification may be obtained by replacing at least one nucleotide included in the nucleic acid molecule by any one of LNA (locked nucleic acid), UNA (unlocked nucleic acid), morpholino and PNA (peptide nucleic acid). In addition, the chemical modification may be obtained by binding the nucleic acid molecule to one or more selected from the group consisting of lipids, cell penetrating peptides and cell targeting ligands.

In addition, the nucleic acid molecule according to the present invention may be efficiently used for in vitro and in vivo delivery together with various delivery vehicles, such as liposomes, cationic polymers, antibodies, aptamers or nanoparticles, and delivery methods, known to effectively deliver oligonucleotides into cells.

Meanwhile, in an example of the present invention, it was shown that, when the nucleic acid molecule of the present invention, dissolved in a solution such as PBS, was injected without using a separate delivery vehicle, it exhibited a high gene silencing efficiency of 90% or higher in a target area in vivo, suggesting that the nucleic acid molecule of the present invention can be developed directly into an injectable drug without needing a separate formulation process.

Examples of the present invention propose that the RNAi-inducing nucleic acid molecule according to the present invention exhibits a target gene silencing effect. Thus, in another aspect, the present invention is directed to a gene-silencing composition containing an RNAi-inducing nucleic acid molecule. Herein, the nucleic acid molecule may be contained in the form of a nucleic acid complex comprising a cell delivery vehicle bound thereto.

In an example of the present invention, it was found that, when the nucleic acid structure of the present invention was applied to an siRNA targeting the target gene CTGF, the efficiency with which the expression of the target gene is inhibited could be significantly increased, and the cell-penetrating ability thereof could also be maintained for a long period of time. Thus, it will be obvious to those skilled in the art that, even when nucleic acid molecules targeting other target genes are provided according to the present invention, the same results can be obtained.

Meanwhile, the composition for inhibiting gene expression according to the present invention may be provided in the form of a kit for inhibiting gene expression. The kit for inhibiting gene expression may take the form of bottles, tubs, sachets, envelops, tubes, ampoules, and the like, which may be formed in part or in whole from plastic, glass, paper, foil, wax, and the like. The container may be equipped with a fully or partially detachable lid that may initially be part of the container or may be affixed to the container by mechanical, adhesive, or other means. The container may also be equipped with a stopper, allowing access to the contents by a syringe needle. The kit may comprise an exterior package which may include instructions regarding the use of the components.

In still another aspect, the present invention is directed to a method of inhibiting expression of a target gene in a cell using the above RNAi-inducing nucleic acid molecule. That is, the present invention is directed to a method for inhibiting expression of a target gene in a cell, which comprises a step of introducing the above RNAi-inducing nucleic acid molecule into a cell.

In the present invention, the first strand of the RNAi-inducing nucleic acid may be complementary to the mRNA sequence of a target gene.

In the present invention, the target gene may be an endogeneous gene or a transgene.

The nucleic acid molecule according to the present invention is not necessarily limited to a synthetic siRNA and can also advantageously be applied to siRNA or shRNA, which is expressed in cells using an expression vector or the like. In other words, the nucleic acid molecule of the present invention can be expressed in cells to inhibit the expression of the target gene. Thus, in still another aspect, the present invention is directed to a method for inhibiting expression of a target gene in a cell, the method comprising a step of expressing the above RNAi-inducing nucleic acid molecule in the cell.

Meanwhile, the nucleic acid molecule according the present invention can target an mRNA encoding a connective tissue growth factor (CTGF). In an example of the present invention, it was found that the expression of CTGF was inhibited through the introduction of the nucleic acid molecule having the structure according to the present invention into the cell. Thus, in yet another aspect, the present invention is directed to a pharmaceutical composition for treating or preventing a connective tissue growth factor (CTGF)-associated disease or disorder, the composition containing the above nucleic acid molecule that targets a CTGF-encoded mRNA. The present invention is directed to a method of treating or preventing a connective tissue growth factor (CTGF)-associated disease or disorder comprising administering a pharmaceutical composition containing the above nucleic acid molecule targeting a CTGF-encoding mRNA.

In addition, the nucleic acid molecule of the present invention can be developed into therapeutic agents against localized diseases, and may be used together with various known cell-specific antibodies, aptamers, ligands or the like, and thus can be developed into therapeutic agents for gene regulation, which exhibit gene silencing effects only in a desired area.

The anticancer composition of the present invention may be provided as a pharmaceutical composition comprising the RNAi-inducing nucleic acid molecule alone or in combination with at least one pharmaceutically acceptable carrier, excipient or diluent. The nucleic acid molecule may be contained in the pharmaceutical composition in a pharmaceutically effective amount according to a disease and the severity thereof, the patient's age, weight, health condition and sex, the route of administration and the period of treatment.

As used herein, the term "pharmaceutically acceptable composition" refers to a composition that is physiologically acceptable and does not cause gastric disorder, allergic reactions such as gastrointestinal disorder or vertigo, or similar reactions, when administered to humans. Examples of said carrier, excipient or diluent may include lactose, dextrose, sucrose, sorbitol, mannitol, xylitol, erythritol, maltitol, starch, acacia rubber, alginate, gelatin, calcium phosphate, calcium silicate, cellulose, methyl cellulose, polyvinylpyrrolidone, water, methylhydroxybenzoate, propylhydroxybenzoate, magnesium stearate and mineral oils.

The pharmaceutical composition may additionally contain fillers, anti-aggregating agents, lubricants, wetting agents, perfumes, emulsifiers and preservatives. Also, the pharmaceutical composition of the present invention may be formulated using a method well known in the art, such that it can provide the rapid, sustained or delayed release of the active ingredient after administration to mammals. The formulation may be in the form of sterile injection solutions, etc.

EXAMPLES

Hereinafter, the present invention will be described in further detail with reference to examples. It will be obvious to a person having ordinary skill in the art that these examples are illustrative purposes only and are not to be construed to limit the scope of the present invention. In addition, it will be apparent to those skilled in that art that various modifications and variations can be made without departing from the technical scope of the present invention based on this illustration.

Example 1: Screening of RNAi-Inducing Double Stranded Nucleic Acid Molecules Targeting CTGF Before introduction of various chemical modifications for effective self-delivery structures, in order to secure highly efficient, RNAi-inducing double-stranded nucleic acid molecules targeting CTGF, 50 sequences targeting CTGF were designed, followed by screening.

To compare CTGF gene-silencing efficiency between lasiRNA and conventional RNAi-inducing structures, the siRNA, asiRNA and lasiRNA structures having the nucleotide sequences shown in Tables 1 to 3 below were synthesized. Tables 1 to 3 show 24 nucleotide sequences for each of the siRNA, asiRNA and lasiRNA structures that target CTGF (Capital letters: RNA; small letters: DNA). To test the CTGF mRNA silencing effect of each of the structures having the nucleotide sequences, each of the structures was transfected into HaCaT (ATCC) cells at a concentration of 10 nM, and then the expression levels of CTGF mRNA in the cells were measured by real-time PCR.

TABLE 1

| No | siRNA NAME | SEQ | | Sequence (5'→3') |
|---|---|---|---|---|
| No1 | siRNA | 1 | sense | GCGAGGAGUGGGUGUGUGAtt |
| | | 2 | antisense | UCCUCGCAGCAUUUCCCGGtt |
| | asiRNA | 3 | sense | AGGAGUGGGUGUGUGA |
| | | 4 | antisense | UCCUCGCAGCAUUUCCCGGtt |
| | lasiRNA | 5 | sense | AGGAGUGGGUGUGUGA |
| | | 6 | antisense | UCACACACCCACUCCUCGCAGCAUUUCCCGG |
| No2 | siRNA | 7 | sense | AGACCUGUGGGAUGGGCAUtt |
| | | 8 | antisense | CAGGUCUUGGAACAGGCGCtt |
| | asiRNA | 9 | sense | CCUGUGGGAUGGGCAU |
| | | 10 | antisense | CAGGUCUUGGAACAGGCGCtt |
| | lasiRNA | 11 | sense | CCUGUGGGAUGGGCAU |
| | | 12 | antisense | AUGCCCAUCCCACAGGUCUUGGAACAGGCGC |
| No3 | siRNA | 13 | sense | ACAGGAAGAUGUACGGAGAtt |
| | | 14 | antisense | UUCCUGUAGUACAGCGAUUtt |
| | asiRNA | 15 | sense | GGAAGAUGUACGGAGA |
| | | 16 | antisense | UUCCUGUAGUACAGCGAUUtt |
| | lasiRNA | 17 | sense | GGAAGAUGUACGGAGA |
| | | 18 | antisense | UCUCCGUACAUCUUCCUGUAGUACAGCGAUU |
| No4 | siRNA | 19 | sense | GCACCAGCAUGAAGACAUAtt |
| | | 20 | antisense | UAUGUCUUCAUGCUGGUGCtt |
| | asiRNA | 21 | sense | CCAGCAUGAAGACAUA |
| | | 22 | antisense | UAUGUCUUCAUGCUGGUGCtt |

TABLE 1-continued

| No | siRNA NAME | SEQ | | Sequence (5'→3') |
|---|---|---|---|---|
| | 1asiRNA | 23 | sense | CCAGCAUGAAGACAUA |
| | | 24 | antisense | UAUGUCUUCAUGCUGGUCCAGCCAGAAAGCU |
| No5 | siRNA | 25 | sense | GAAGACAUACCGAGCUAAAtt |
| | | 26 | antisense | UUUAGCUCGGUAUGUCUUCtt |
| | asiRNA | 27 | sense | GACAUACCGAGCUAAA |
| | | 28 | antisense | UUUAGCUCGGUAUGUCUUCtt |
| | 1asiRNA | 29 | sense | GACAUACCGAGCUAAA |
| | | 30 | antisense | UUUAGCUCGGUAUGUCUUCAUGCUGGUGCAG |
| No6 | siRNA | 31 | sense | GCUAAAUUCUGUGGAGUAUtt |
| | | 32 | antisense | AUACUCCACAGAAUUUAGCtt |
| | asiRNA | 33 | sense | AAAUUCUGUGGAGUAU |
| | | 34 | antisense | AUACUCCACAGAAUUUAGCtt |
| | 1asiRNA | 35 | sense | AAAUUCUGUGGAGUAU |
| | | 36 | antisense | AUACUCCACAGAAUUUAGCUCGGUAUGUCUU |
| No7 | siRNA | 37 | sense | GCGAGGUCAUGAAGAAGAAtt |
| | | 38 | antisense | UUGUUCUUCAUGACCUCGCtt |
| | asiRNA | 39 | sense | AGGUCAUGAAGAAGAA |
| | | 40 | antisense | UUGUUCUUCAUGACCUCGCtt |
| | 1asiRNA | 41 | sense | AGGUCAUGAAGAAGAA |
| | | 42 | antisense | UUGUUCUUCAUGACCUCGCCGUCAGGGCACU |
| No8 | siRNA | 43 | sense | UGGAAGAGAACAUUAAGAAtt |
| | | 44 | antisense | UUCUUAAUGUUCUCUUCCAtt |
| | asiRNA | 45 | sense | AAGAGAACAUUAAGAA |
| | | 46 | antisense | UUCUUAAUGUUCUCUUCCAtt |
| | 1asiRNA | 47 | sense | AAGAGAACAUUAAGAA |
| | | 48 | antisense | UUCUUAAUGUUCUCUUCCAGGUCAGCUUCGC |

(Capital letters: RNA; small letters: DNA)

TABLE 2

| No | siRNA NSA | | Sequence (5'→3') |
|---|---|---|---|
| No9 | siRNA | (49) sense | CGGCUUACCGACUGGAAGAtt |
| | | (50) antisense | UCUUCCAGUCGGUAAGCCGtt |
| | asiRNA | (51) sense | CUUACCGACUGGAAGA |
| | | (52) antisense | UCUUCCAGUCGGUAAGCCGtt |
| | 1asiRNA | (53) sense | CUUACCGACUGGAAGA |
| | | (54) antisense | UCUUCCAGUCGGUAAGCCGCGAGGGCAGGCC |
| No10 | siRNA | (55) sense | GCAUGAAGCCAGAGAGUGAtt |
| | | (56) antisense | UCACUCUCUGGCUUCAUGCtt |

TABLE 2-continued

| No | siRNA NSA | | Sequence (5'→3') |
|---|---|---|---|
| | asiRNA | (57) sense | UGAAGCCAGAGAGUGA |
| | | (58) antisense | UCACUCUCUGGCUUCAUGCtt |
| | lasiRNA | (59) sense | UGAAGCCAGAGAGUGA |
| | | (60) antisense | UCACUCUCUGGCUUCAUGCCCAUGUCUCCGU |
| No11 | siRNA | (61) sense | CACCAUAGGUAGAAUGUAAtt |
| | | (62) antisense | UUACAUUCUACCUAUGGUGtt |
| | asiRNA | (63) sense | CAUAGGUAGAAUGUAA |
| | | (64) antisense | UUACAUUCUACCUAUGGUGtt |
| | lasiRNA | (65) sense | CAUAGGUAGAAUGUAA |
| | | (66) antisense | UUACAUUCUACCUAUGGUGUUCAGAAAUUGA |
| No12 | siRNA | (67) sense | CCUGCAGGCUAGAGAAGCAtt |
| | | (68) antisense | UGCUUCUCUAGCCUGCAGGtt |
| | asiRNA | (69) sense | GCAGGCUAGAGAAGCA |
| | | (70) antisense | UGCUUCUCUAGCCUGCAGGtt |
| | lasiRNA | (71) sense | GCAGGCUAGAGAAGCA |
| | | (72) antisense | UGCUUCUCUAGCCUGCAGGAGGCGUUGUCAU |
| No13 | siRNA | (73) sense | CCAGAGAGUGAGAGACAUUtt |
| | | (74) antisense | AAUGUCUCUCACUCUCUGGtt |
| | asiRNA | (75) sense | GAGAGUGAGAGACAUU |
| | | (76) antisense | AAUGUCUCUCACUCUCUGGtt |
| | lasiRNA | (77) sense | GAGAGUGAGAGACAUU |
| | | (78) antisense | AAUGUCUCUCACUCUCUGGCUUCAUGCCAUG |
| No14 | siRNA | (79) sense | GCGAAGCUGACCUGGAAGAtt |
| | | (80) antisense | UCUUCCAGGUCAGCUUCGCtt |
| | asiRNA | (81) sense | AAGCUGACCUGGAAGA |
| | | (82) antisense | UCUUCCAGGUCAGCUUCGCtt |
| | lasiRNA | (83) sense | AAGCUGACCUGGAAGA |
| | | (84) antisense | UCUUCCAGGUCAGCUUCGCAAGGCCUGACCA |
| No15 | siRNA | (85) sense | CCGGAGACAAUGACAUCUUtt |
| | | (86) antisense | AAGAUGUCAUUGUCUCCGGtt |
| | asiRNA | (87) sense | GAGACAAUGACAUCUU |
| | | (88) antisense | AAGAUGUCAUUGUCUCCGGtt |
| | lasiRNA | (89) sense | GAGACAAUGACAUCUU |
| | | (90) antisense | AAGAUGUCAUUGUCUCCGGGACAGUUGUAAU |
| No16 | siRNA | (91) sense | UCUUUGAAUCGCUGUACUAtt |
| | | (92) antisense | UAGUACAGCGAUUCAAAGAtt |
| | asiRNA | (93) sense | UUGAAUCGCUGUACUA |
| | | (94) antisense | UAGUACAGCGAUUCAAAGAtt |

TABLE 2-continued

| No | siRNA NSA | Sequence (5'→3') |
|---|---|---|
| | lasiRNA (95) sense | UUGAAUCGCUGUACUA |
| | (96) antisense | UAGUACAGCGAUUCAAAGAUGUCAUUGUCUC |

(Capital letters: RNA; small letters: DNA)

TABLE 3

| No | siRNA NAME | SEQ ID NO | | Sequence (5'→3') |
|---|---|---|---|---|
| No17 | siRNA | 97 | sense | UUGCGAAGCUGACCUGGAAtt |
| | | 98 | antisense | UUCCAGGUCAGCUUCGCAAtt |
| | asiRNA | 99 | sense | CGAAGCUGACCUGGAA |
| | | 100 | antisense | UUCCAGGUCAGCUUCGCAAtt |
| | lasiRNA | 101 | sense | CGAAGCUGACCUGGAA |
| | | 102 | antisense | UUCCAGGUCAGCUUCGCAAGGCCUGACCAUG |
| No18 | siRNA | 103 | sense | CAACUAUGAUUAGAGCCAAtt |
| | | 104 | antisense | UUGGCUCUAAUCAUAGUUGtt |
| | asiRNA | 105 | sense | CUAUGAUUAGAGCCAA |
| | | 106 | antisense | UUGGCUCUAAUCAUAGUUGtt |
| | lasiRNA | 107 | sense | CUAUGAUUAGAGCCAA |
| | | 108 | antisense | UUGGCUCUAAUCAUAGUUGGGUCUGGGCCAA |
| No19 | siRNA | 109 | sense | GUACCAGUGCACGUGCCUGtt |
| | | 110 | antisense | CAGGCACGUGCACUGGUACtt |
| | asiRNA | 111 | sense | CCAGUGCACGUGCCUG |
| | | 112 | antisense | CAGGCACGUGCACUGGUACtt |
| | lasiRNA | 113 | sense | CCAGUGCACGUGCCUG |
| | | 114 | antisense | CAGGCACGUGCACUGGUACUUGCAGCUGCUC |
| No20 | siRNA | 115 | sense | AGUGCAUCCGUACUCCCAAtt |
| | | 116 | antisense | UUGGGAGUACGGAUGCACUtt |
| | asiRNA | 117 | sense | GCAUCCGUACUCCCAA |
| | | 118 | antisense | UUGGGAGUACGGAUGCACUtt |
| | lasiRNA | 119 | sense | GCAUCCGUACUCCCAA |
| | | 120 | antisense | UUGGGAGUACGGAUGCACUUUUUGCCCUUCU |
| No21 | siRNA | 121 | sense | CAUGAUGUUCAUCAAGACCtt |
| | | 122 | antisense | GGUCUUGAUGAACAUCAUGtt |
| | asiRNA | 123 | sense | GAUGUUCAUCAAGACC |
| | | 124 | antisense | GGUCUUGAUGAACAUCAUGtt |
| | lasiRNA | 125 | sense | GAUGUUCAUCAAGACC |
| | | 126 | antisense | GGUCUUGAUGAACAUCAUGUUCUUCUUCAUG |
| No22 | siRNA | 127 | sense | CCAUGACCGCCGCCAGUAUtt |
| | | 128 | antisense | AUACUGGCGGCGGUCAUGGtt |

TABLE 3-continued

| No | siRNA NAME | SEQ ID NO | | Sequence (5'→3') |
|---|---|---|---|---|
| | asiRNA | 129 | sense | UGACCGCCGCCAGUAU |
| | | 130 | antisense | AUACUGGCGGCGGUCAUGGtt |
| | lasiRNA | 131 | sense | UGACCGCCGCCAGUAU |
| | | 132 | antisense | AUACUGGCGGCGGUCAUGGUUGGCACUGCGG |
| No23 | siRNA | 133 | sense | GAACAUUAAGAAGGGCAAAtt |
| | | 134 | antisense | UUUGCCCUUCUUAAUGUUCtt |
| | asiRNA | 135 | sense | CAUUAAGAAGGGCAAA |
| | | 136 | antisense | UUUGCCCUUCUUAAUGUUCtt |
| | lasiRNA | 137 | sense | CAUUAAGAAGGGCAAA |
| | | 138 | antisense | UUUGCCCUUCUUAAUGUUCUCUUCCAGGUCA |
| No24 | siRNA | 139 | sense | GGAAGACACGUUUGGCCCAtt |
| | | 140 | antisense | UGGGCCAAACGUGUCUUCCtt |
| | asiRNA | 141 | sense | AGACACGUUUGGCCCA |
| | | 142 | antisense | UGGGCCAAACGUGUCUUCCtt |
| | lasiRNA | 143 | sense | AGACACGUUUGGCCCA |
| | | 144 | antisense | UGGGCCAAACGUGUCUUCCAGUCGGUAAGCC |

(Capital letters: RNA; small letters: DNA)

Specifically, HaCat cells were cultured in Dulbecco's modified Eagle's medium (Gibco) (supplemented with 10% fetal bovine serum (Gibco) and 100 µg/ml penicillin/streptomycin) in a 100 mm Petri dish. Immediately before transfection, $8\times10^4$ Hacat cells were seeded into a 12-well plate. Meanwhile, each of the siRNA, asiRNA and lasiRNA was diluted in 1× siRNA duplex buffer (Biosesang Co., Ltd.) at a suitable concentration, and incubated at 90° C. for 2 min and at 37° C. for 1 hour. The annealed siRNAs were electrophoresed on 10% polyacrylamide gel, and then stained with EtBr for 5 min, and the bands were visualized by a UV transilluminator. The siRNAs were transfected into the cells according to the manual provided in Lipofectamine 2000 (Invitrogen), and after 24 hours, the mRNA levels in the cells were measured.

Specifically, after transfection, total RNA was extracted using Isol-RNA lysis reagent (5PRIME), and 500 ng of the RNA was used for cDNA synthesis. cDNA was synthesized using a high-capacity cDNA reverse transcription kit (Applied Biosystems) according to the protocol provided in the kit. The synthesized cDNA was diluted, and then subjected to quantitative real-time PCR using a step one real-time PCR system (Applied Biosystems) according to the protocol provided in the system. The target gene was analyzed using a power SYBR green PCR master mix (Applied Biosystems) with gene-specific primers. The nucleotide sequences of the primers used in the experiment are as follows:

GAPDH-forward
(SEQ ID NO: 145)
5'-GAG TCA ACG GAT TTG GTC GT-3'

GAPDH-reverse
(SEQ ID NO: 146)
5'-GAC AAG CTT CCC GTT CTC AG-3'

CTGF-forward
(SEQ ID NO: 147)
5'-CAA GGG CCT CTT CTG TGA CT-3'

CTGF-reverse
(SEQ ID NO: 148)
5'-ACG TGC ACT GGT ACT GCA G-3'

FIG. 1 shows the results of screening of 24 nucleotide sequences. As shown therein, in 14 sequences among a total of 24 nucleotide sequences, lasiRNAs showed increased activity compared to siRNAs (lasiRNAs showed an increase in gene silencing efficiency of 20% or higher compared to siRNA), and in 5 sequences, siRNAs showed high gene silencing efficiency compared to lasiRNAs, suggesting that lasiRNAs generally show high gene silencing efficiency compared to conventional siRNAs.

Particularly, the IC50 of the siRNAs and lasiRNA showing a gene silencing efficiency of 90% or higher was measured, and as a result, it was shown that lasiRNAs having nucleotide sequences of Nos. 9 and 16 had the lowest IC50. Among them, the nucleotide sequence of No. 9 was selected as a final candidate for modification and self-delivery experiments. Information about the nucleotide sequence of No. 9 is shown in Table 4 below.

TABLE 4

RNAi-inducing double-stranded nucleic acid molecule

| siRNA No | name | | Sequence (5' -> 3') | Sequence listing |
|---|---|---|---|---|
| No9 siRNA | sense | | CGGCUUACCGACUGGAAGAtt | 149 |
| | antisense | | UCUUCCAGUCGGUAAGCCGtt | 150 |
| asiRNA | sense | | CUUACCGACUGGAAGA | 151 |
| | antisense | | UCUUCCAGUCGGUAAGCCGtt | 152 |
| lasiRNA | sense | | CUUACCGACUGGAAGA | 153 |
| | antisens | | UCUUCCAGUCGGUAAGCCGCGAGGGCAGGCC | 154 |

(Capital letters: RNA; small letters: DNA)

Example 2: Preparation of Nucleic Acid Molecule According to the Present Invention, and Measurement of Intracellular Uptake Efficiency Thereof 2-1: Effect of Cholesterol Modification In order to examine the effect of cholesterol modification on the delivery of lasiRNA, the 5' end of the lasiRNA sense strand, that is, the second strand, was labeled with cy3, and then the difference in uptake of lasiRNA between the presence and absence of cholesterol was observed by a fluorescence microscope. Specifically, the cy3-labeled lasiRNA or chol-lasiRNA structure was incubated in HeLa cells at a concentration of 1 µM for 3 hours, and then the degree of intracellular delivery thereof was measured by observation with a fluorescence microscope.

Specifically, HeLa cells (ATCC) were cultured in Dulbecco's modified Eagle's medium (Gibco) (supplemented with 10% fetal bovine serum (Gibco) and 100 µg/ml penicillin/streptomycin) in a 100 mm Petri dish.

Each of cholesterol-modified lasiRNAs was diluted in single-strand Accell siRNA delivery medium (Thermo scientific) at a suitable concentration, and the cholesterol-modified single strand was incubated at 90° C. for 20-30 sec before annealing. The sense strand and the antisense strand were mixed with each other, and then incubated at 90 for 30 sec and at 37° C. for 1 hour, followed by annealing. The resulting siRNAs were electrophoresed on 10% polyacrylamide gel, and then stained with EtBr for 5 min, and the bands were visualized by a UV transilluminator.

For an incubation test, $2\times10^5$ HeLa cells were seeded into a cover glass-bottom dish (SPL) at 24 hours before treatment with lasiRNA. After removal of culture media from the prepared dish, the cells were washed twice with 2 ml of 1×DPBS. siRNA, diluted in 100 µL of Accell siRNA delivery medium (Thermo scientific) pre-warmed in a water bath at 37° C., was added to and incubated in the cells. After 3 hours, the Accell medium was removed, and the cells were washed twice with 1×DPBS, and then incubated with 1 µg/ml of Hoechst 33343 (Sigma) in Opti-MEM (gibco) at 37° C. for 10 min to stain the nucleus. After removal of the Hoechst, the cells were washed twice with 1×DPBS, and then added to Opti-MEM medium and observed with a fluorescence microscope (Microscope-Olympus IX81, software—MetaMorph).

Figure 2:
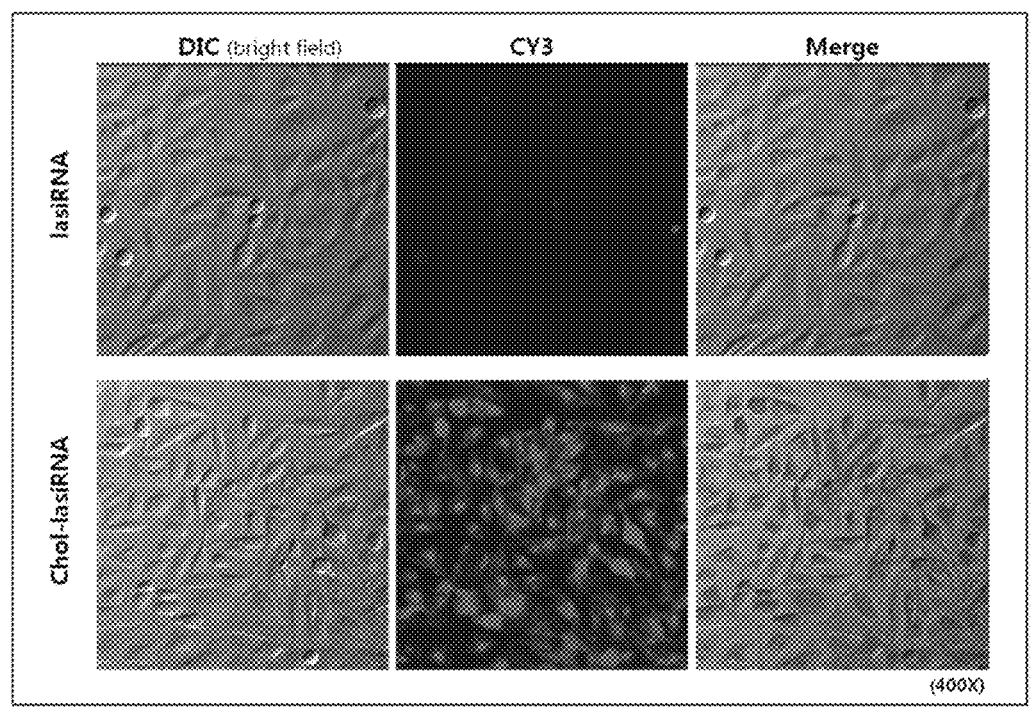
FIG. 2 depicts fluorescence micrographs showing the increase in intracellular uptake efficiency of lasiRNA by cholesterol modification.

As can be seen in FIG. 2, when the intracellular uptake efficiency of cholesterol-modified lasiRNA was examined, and as a result, it could be seen that little or no cy3 fluorescence was observed in the cells in the absence of cholesterol, but lasiRNA-chol obtained by conjugating cholesterol to lasiRNA showed very strong fluorescence.

This suggests that the intracellular delivery of the lasiRNA structure was increased by cholesterol modification.

2-2: Effect of PS Modification

Additionally, in order to examine whether the direct introduction of phosphorothioate (PS) modification into lasiRNA increases the uptake efficiency of the lasiRNA, PS modification was introduced into the 3' overhang of the antisense strand (i.e., first strand) of chol-lasiRNA, and the change in uptake efficiency of the chol-lasiRNA by PS modification was tested. Each of cy3-labelled chol-lasiRNA-PS(N) structures was incubated in HeLa cells at a concentration of 1 µM for 3 hours, and then the degrees of intracellular delivery of the structures was compared by observation with a fluorescence microscope. For an accurate comparison between cell penetrating abilities between the structures, the condition in which chol-lasiRNA-PS0 shows the lowest fluorescence was set, after which the fluorescence intensities of other structures were compared.

Specifically, as shown in FIG. 3, 0, 4, 7, 12 or 17 PS modification(s) were introduced into the 3' end of the antisense strand of the Chol-lasiRNA structure, which was then incubated in or transfected into HeLa cells. Then, as described in Example 2-1, the difference in delivery efficiency by the number of PS modifications was observed with a fluorescence microscope. In FIG. 3, the underline and the red color represent OMe modification, * represents PS modification, Chol represents cholesterol, and Cy3 represents Cy3 fluorescent dye.

Figure 4:
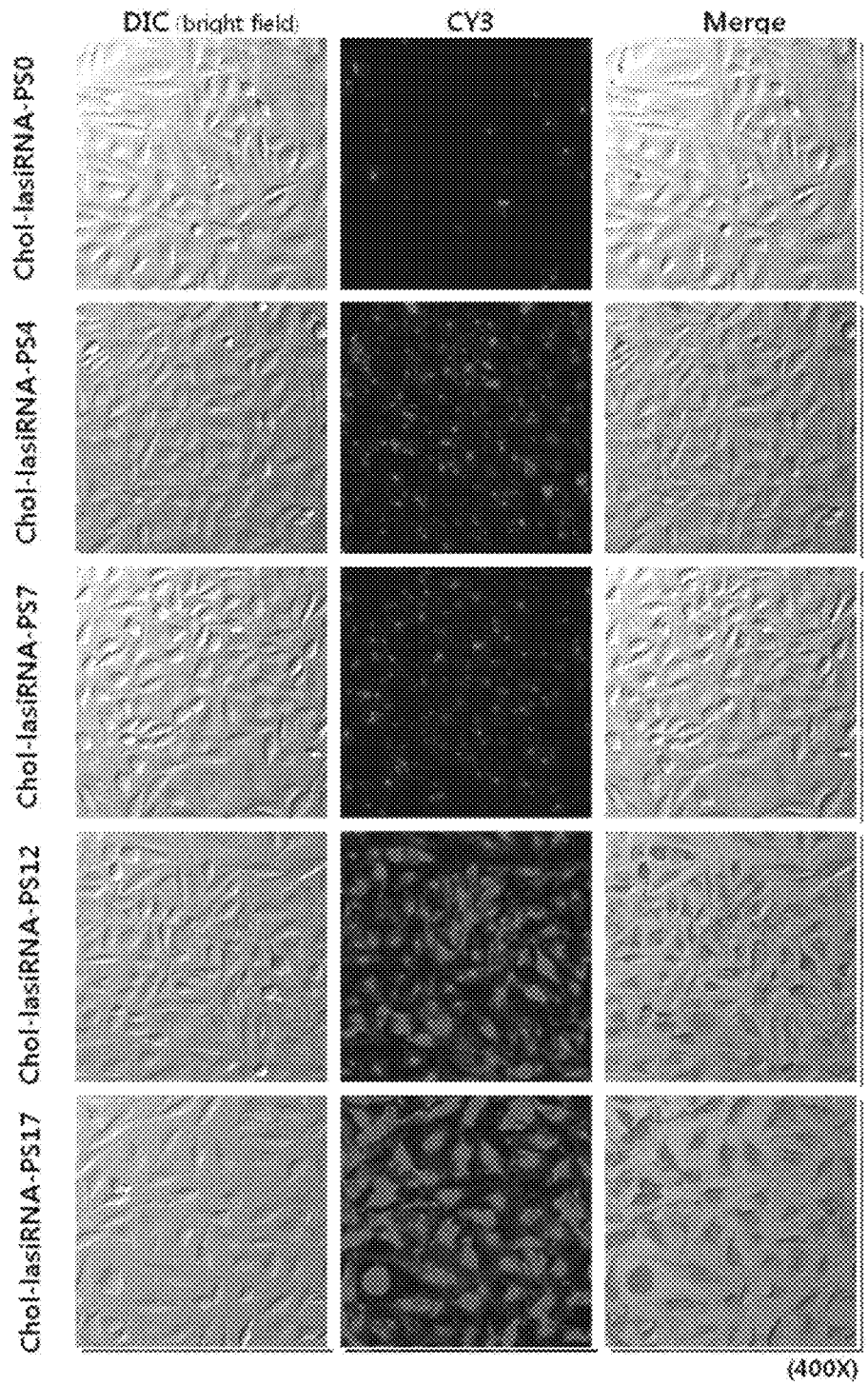
FIG. 4 depicts fluorescence micrographs showing the increase in intracellular uptake efficiency of chol-lasiRNA by phosphorothioate (PS) modification.

As a result, as shown in FIG. 4, in the case of chol-lasiRNA-PS0 having no PS modification, little or no fluorescence was observed in the HeLa cells, and chol-lasiRNA-PS0 showed low uptake efficiency compared to other samples.

In addition, it was observed that fluorescence became brighter as the number of PS modifications in the antisense strand (i.e., first strand) of lasiRNA increased, and among all the samples, chol-lasiRNA-PS12 and chol-lasiRNA-PS17 having 12 and 17 PS modifications, respectively, showed the brightest fluorescence, indicating that the amount of internalized lasiRNA increased with an increase in the number of PS modifications in chol-lasiRNA.

Example 3: Measurement of CTGF-Silencing Efficiency

The results of the internalization experiment carried out using Cy3-labeled lasiRNA in Example 2 indicated that the direct introduction of cholesterol and PS modifications into the lasiRNA structure enables the lasiRNA to be effectively delivered into cells without needing a delivery vehicle or an additional reagent. However, it is known that when various chemical modifications are introduced into siRNA, the activity of the siRNA somewhat decreases, or the activity of siRNA decreases rapidly depending on the kind of modification. Thus, in order to examine the effect of each modification on the activity of lasiRNA, various lasiRNA structures were transfected into HeLa cells, and then a change in the expression of CTGF mRNA in the cells was measured to determine the effect of each of the modifications on the gene silencing efficiency of the lasiRNA.

In order to examine the effect of PS modification on the gene silencing efficiency of lasiRNA, various PS-modified lasiRNA [chol-lasiRNA-PS(N)] structures were transfected into HeLa cells, and then the expression levels of the CTGF gene in the cells were measured. Specifically, each of chol-lasiRNA-PS(N) structures was transfected into HeLa cells at a concentration of 10 nM, and after 48 hours, the expression levels of CTGF mRNA in the cells were measured by real-time PCR.

Subsequently, at 24 hours before the experiment, $2.5 \times 10^4$ HeLa cells were seeded into a 24-well plate. Then, each of the lasiRNAs was transfected using Lipofectamine 2000 according to the protocol provided therein. Next, the cells were cultured in a 5% $CO_2$ incubator for 48 hours, and then the expression level of mRNA in the cells was measured according to the method described in Example 1.

Figure 5:
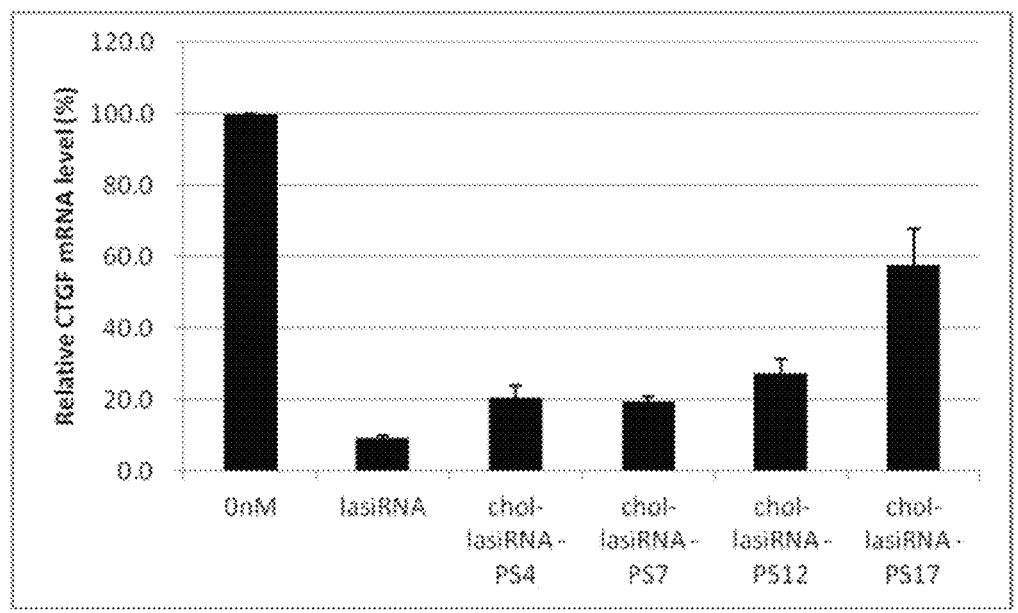
FIG. 5 is a graphic diagram showing a comparison between the gene silencing effects of chol-lasiRNAs according to variation of numbers in phosphorothioate (PS) modifications. Each graph represents the mean±SD of three repeated experiments.

As a result, as shown in FIG. 5, the gene silencing efficiency of the lasiRNAs showed a tendency to decrease as the number of PS modifications in the antisense strand increased, and when 12 or more PS modifications were introduced into the antisense strand, a slight decrease in the silencing activity was observed. Also, it was shown that chol-lasiRNA-PS17 having 17 PS modifications introduced into the antisense strand showed significantly low gene silencing efficiency, and thus showed little or no silencing effect on CTGF, suggesting that the number of PS modifications in the antisense strand is preferably 17 or less, and that 17 or more PS modifications are not suitable for self-delivery of the lasiRNA. Each graph in FIG. 5 represents the mean±SD of three repeated experiments.

Additionally, an increase in the number of PS modifications leads to an increase in the self-delivery efficiency of chol-lasiRNA, but has the disadvantage of reducing the silencing activity of the lasiRNA. In order to establish the optimum modification structure enabling silencing to be induced without needing a vehicle, chol-lasiRNA-PS(N) structures having varying numbers of PS modifications were incubated with HeLa cells, and then the CTGF mRNA levels of the cells were measured to compare the gene silencing efficiencies of the structures. Herein, the cells were treated with 0.1 μM, 0.3 μM and 1 μM of each of the lasiRNAs, and chol-lasiRNA-PS7 (FIG. 6; red: OMe modification; *: PS modification; Chol: cholesterol) targeting MyD88 was also used as a control. Specifically, HeLa cells were incubated with CTGF- or MyD88-targeting chol-lasiRNA-PS(N) structures for 48 hours, and then the expression levels of CTGF mRNA in the cells were measured by real-time PCR.

Figure 7:
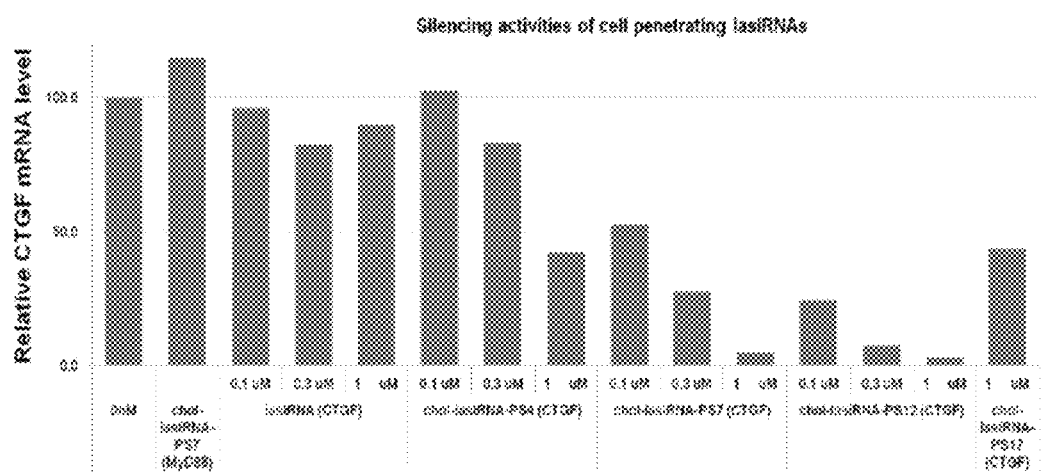
FIG. 7 is a graphic diagram showing a comparison between the gene silencing efficiencies of a variety of cell-penetrating lasiRNAs (cp-lasiRNAs). The parenthesized CTGF or MyD88 represents a gene that is targeted by cp-lasiRNAs.

As a result, as can be seen in FIG. 7, chol-lasiRNA-PS4 showed a gene silencing effect of only about 55% even at the highest concentration (1 μM), and chol-lasiRNA-PS7 and chol-lasiRNA-PS12 showed a CTGF silencing effect of about 95% or higher at 1 μM. For a more accurate comparison of gene silencing efficiency, each of the structures was incubated at lower concentrations, and then the CTGF mRNA level was measured, and the results of the measurement indicated that PS12 most efficiently silenced the CTGF gene even at low concentrations. In addition, it was observed that chol-lasiRNA-PS17 had a gene silencing effect of about 50% even when it was incubated at a high concentration (1 μM), like when it was transfected, suggesting that it is required to optimize the number of PS modifications suitable for increasing the delivery and silencing activity, rather than to introduce a too large number of PS modifications. In addition, MyD88-targeting chol-lasiRNA-PS7 showed no CTGF silencing efficiency, indicating that gene silencing by the cp-lasiRNA structures occurs in a sequence-specific manner.

Example 4: Measurement of Intracellular Uptake Efficiencies Resulting from Modifications with Other Lipophilic Compounds In order to examine the effects of lipophilic modifications (hydrophobic modifications) other than cholesterol modification, cp-lasiRNA (cell penetrating lasiRNA) structures according to the present invention, which target survivin gene, were prepared using the following sequences. Herein, cp-lasiRNA-1 has cholesterol conjugated thereto, cp-lasiRNA-2 has conjugated thereto tocopherol in place of cholesterol, and cp-lasiRNA-3 has stearic acid conjugated to the 5' end of the sense strand in place of cholesterol.

<cp-lasiRNA (survivin) 31mer>

```
cp-lasiRNA (survivin) Antisense 31 nt:
                                    (SEQ ID NO: 169)
5' UGAAAAUGUUGAUCUCCUUUCCUAAGA*C*A*T*T 3' cp-lasiRNA (survivin) Sense:
                                    (SEQ ID NO: 170)
5' GAGAUCAACAUUUU*C*A*cholesterol. 3'
```

Underline: OMe modification; *: PS: phosphorothioate bond.

Figure 8:
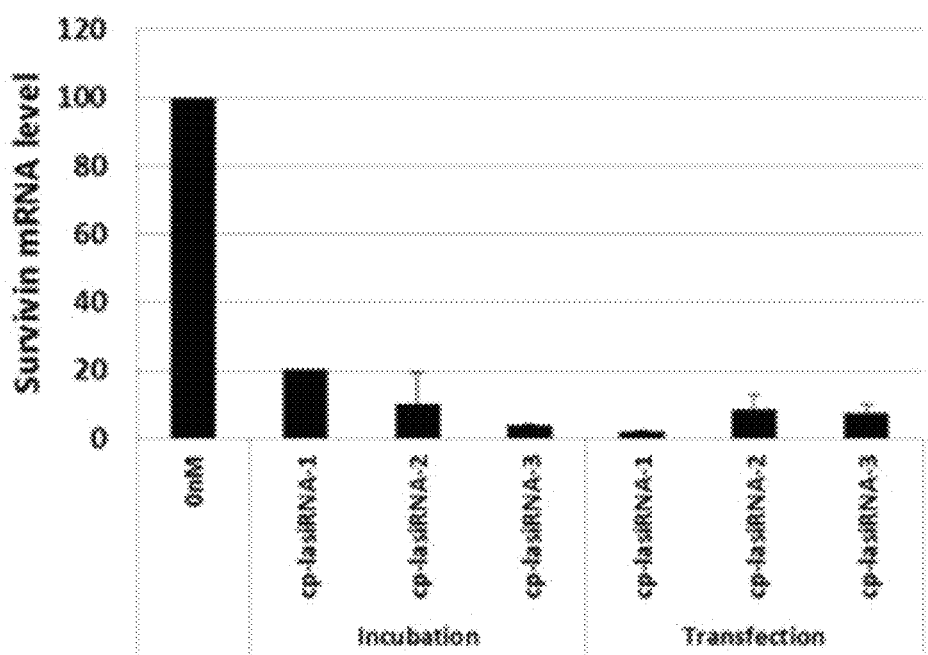
FIG. 8 is a graphic diagram showing the gene silencing efficiencies of the inventive nucleic acid molecules having various lipophilic compound modifications, that is, hydrophobic modifications.

Each of cp-lasiRNA-1, cp-lasiRNA-2 and cp-lasiRNA-3 was incubated in A549 cells (ATCC) at a concentration of 300 mM for 24 hours according to the method described in Example 2, and then the expression levels of survivin mRNA in the cells were measured by real-time PCR. FIG. 8 shows the mean±DS of two repeated experiments for each of the cp-lasiRNA structures.

After transfection, total RNA was extracted using Isol-RNA lysis reagent (5PRIME), and 500 ng of the RNA was used for cDNA synthesis. cDNA was synthesized using a high-capacity cDNA reverse transcription kit (Applied Biosystems) according to the protocol provided therein. The synthesized cDNA was diluted, and then subjected to quantitative real-time PCR using a step one real-time PCR system (Applied Biosystems) according to the protocol provided therein. The target gene was analyzed using a power SYBR green PCR master mix (Applied Biosystems) together with gene-specific primers. The nucleotide sequences of the primers used in the experiment are as follows:

Survivin

```
Forward
                              (SEQ ID NO: 172)
5'-GCA CCA CTT CCA GGG TTT AT-3'

Reverse
                              (SEQ ID NO: 173)
5'-CTC TGG TGC CAC TTT CAA GA-3'
```

As a result, as can be seen in FIG. 8, hydrophobic modifications other than cholesterol modification enabled the target gene to be silenced with high efficiency. In addition, stearyl showed high gene silencing efficiency, even though it was conjugated to the 5' end of the sense strand, suggesting that the nucleic acid molecule according to the present invention can achieve the desired effect even when a lipophilic compound (hydrophobic modification) is conjugated to various positions of the nucleic acid molecule.

Example 5: Examination of Target Gene Silencing Efficiency According to the Length of Antisense Strand In order to examine the target gene silencing efficiency of the inventive nucleic acid molecule according to the length of the first strand thereof, each of 31-nt antisense and 21-nt antisense strands was combined with a 16-nt second strand (sense strand) to make cp-lasiRNAs, and then A549 cells were treated with each of the cp-lasiRNAs.

<cp-lasiRNA (survivin) 31mer>

```
cp-lasiRNA (survivin) Antisense 31 nt:
                              (SEQ ID NO: 169)
5' UGAAAAUGUUGAUCUCCUUUCCUAAGA*C*A*T*T 3' cp-lasiRNA (survivin) Sense:
                              (SEQ ID NO: 170)
5' GAGAUCAACAUUUU*C*A*cholesterol. 3'
```

<cp-lasiRNA (survivin) 21mer>

```
cp-lasiRNA (survivin) Antisense 21 nt:
                              (SEQ ID NO: 171)
5' UGAAAAUGUUGAUCUCCU*U*U*C*C 3' cp-lasiRNA (survivin) Sense:
                              (SEQ ID NO: 170)
5' GAGAUCAACAUUUU*C*A*cholesterol. 3'
```

Underline: OMe modification, *: PS (phosphorothioate bond)

<cp-lasiRNA (CTGF) 31mer>

```
cp-lasiRNA (CTGF) Antisense 31 nt:
                              (SEQ ID NO: 174)
5' UCUUCCAGUCGGUAAGCCGCGAGGGCA*G*G*C*C 3' cp-lasiRNA (CTGF) Sense :
                              (SEQ ID NO: 175)
5' CTTACCGACTGGAA*G*A*chol. 3'
```

<cp-lasiRNA (CTGF) 21mer>

```
cp-lasiRNA (CTGF) Antisense 21 nt:
                              (SEQ ID NO: 176)
5' UCUUCCAGUCGGUAAGC*C*G*C*G 3'
```

```
cp-lasiRNA (CTGF) Sense :
                              (SEQ ID NO: 175)
5' CTTACCGACTGGAA*G*A*chol. 3'
```

Underline: OMe modification, *: PS (phosphorothioate bond)

Figure 9:
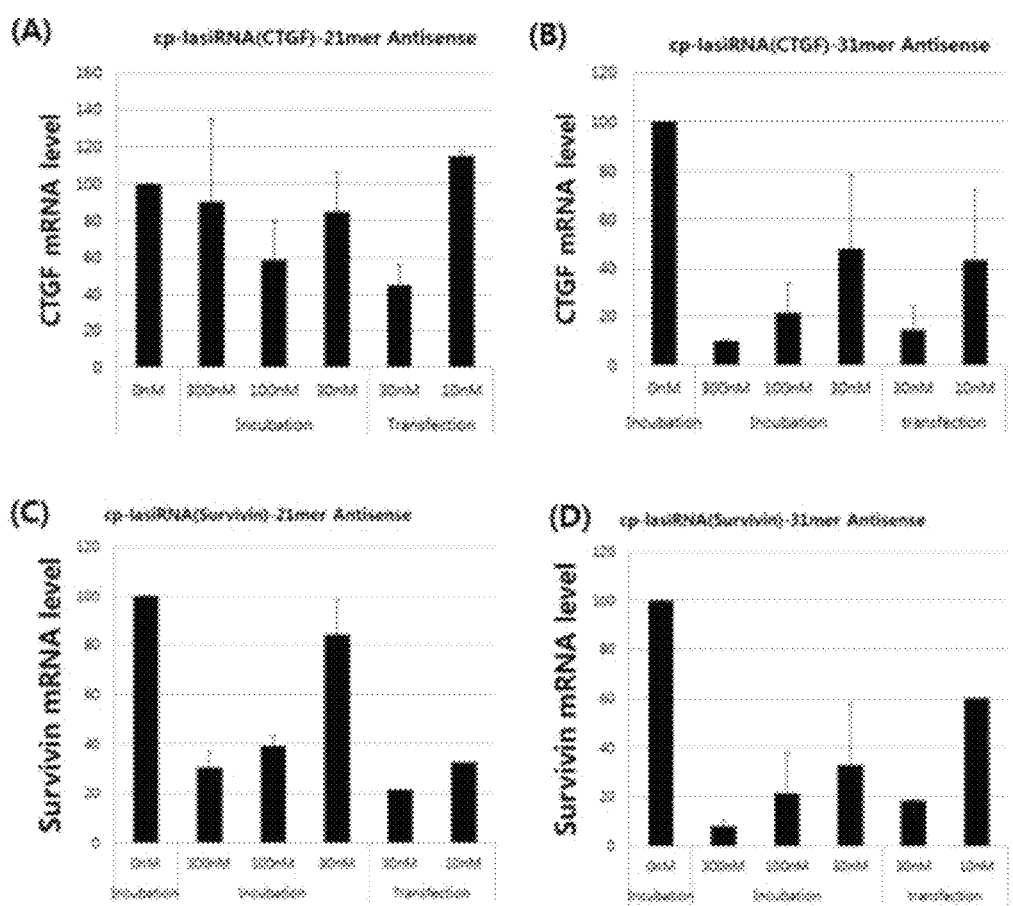
FIG. 9 has four panels (A-D). Panel (A) shows the gene silencing efficiency of a CTGF-targeting cp-asiRNA having a 21 mer antisense strand. Panel (B) shows the gene silencing efficiency of a CTGF-targeting cp-lasiRNA having a 31 mer antisense strand. Panel (C) shows the gene silencing efficiency of a survivin-targeting cp-asiRNA having a 21 mer antisense strand. Panel (D) shows the gene silencing efficiency of a survivin-targeting cp-lasiRNA having a 31 mer antisense strand.

Specifically, each of the nucleic acid molecules was transfected into A549 cells (ATCC) according to the method of Example 1 or incubated in A549 cells for 24 hours according to the method of Example 2. Then, the expression levels of target gene mRNA in the cells were measured by real-time PCR. FIG. 9 shows the mean±SD of two repeated experiments for each of the nucleic acid molecules. Specifically, FIG. 9A shows the gene silencing efficiency of a CTGF-targeting cp-lasiRNA having a 21 mer antisense strand; FIG. 9B shows the gene silencing efficiency of a CTGF-targeting cp-lasiRNA having a 31 mer antisense strand; FIG. 9C shows the gene silencing efficiency of a survivin-targeting cp-lasiRNA having a 21 mer antisense strand; and FIG. 9D shows the gene silencing efficiency of a survivin-targeting cp-lasiRNA having a 31 mer antisense strand. The CTGF silencing efficiency was measured using the primers described in Example 1, and the surviving silencing efficiency was measured using the primers described in Example 4.

As shown in FIG. 9, when the CTGF-targeting cp-lasiRNA was transfected or incubated, the target gene silencing efficiency thereof was higher in the case of the 31-nt antisense stand than in the case of the 21-nt antisense strand (FIGS. 9A and 9B). Likewise, when the surviving-targeting cp-lasiRNA was incubated, the target gene silencing efficiency thereof was higher in the case of the 31-nt antisense strand. Thus, it can be seen that the nucleic acid molecule according to the present invention can be designed to have an antisense strand (i.e., first strand) having varying lengths of 19 nt to 31 nt, and can be used to effectively silence a target gene, but it can more efficiently silence a target gene when it has a 31-nt antisense strand, compared to when it has a 21-nt antisense strand.

Example 6: Examination of Effect of PS2 Modification

The effect of the modification of the phosphate backbone of at least one nucleotide in the nucleic acid molecule with phosphorodithioate (PS2; having a structure shown in FIG. 10) in place of phosphorothioate was examined as follows.

Figure 11:
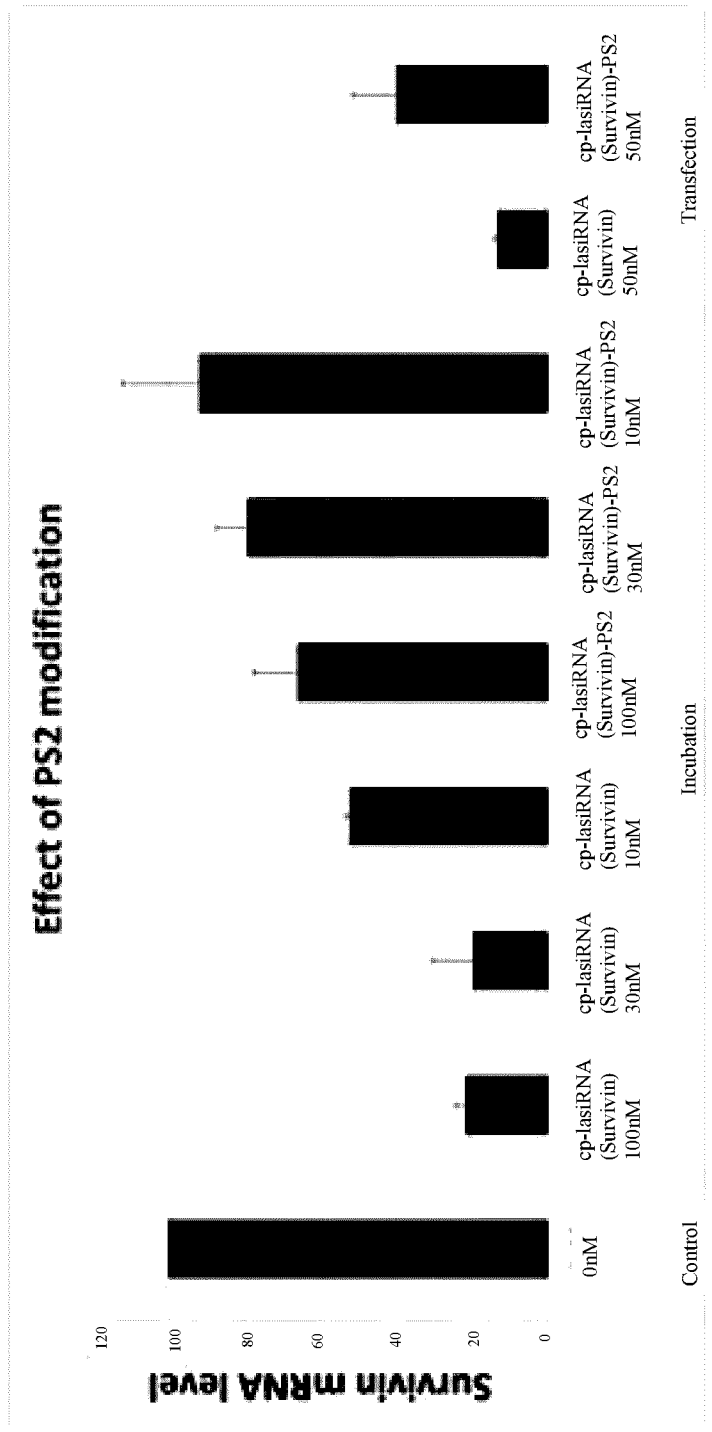
FIG. 11 is a graphic diagram showing the gene silencing efficiencies of the inventive nucleic acid molecules having phosphate backbone modifications.

Specifically, each of the following cp-lasiRNA (Survivin) and the following cp-lasiRNA(Survivin)-PS2, obtained by introducing PS2 modification in place of PS modification into the cp-lasiRNA (survivin), was transfected into or incubated with A549 cells for 24 hours according to the method described in Example 1 or 2. Then, the expression levels of the survivin genes in the cells were measured by real-time PCR in the same manner as described in Example 4. Each graph in FIG. 11 represents the mean±SD of two repeated experiments for each of the cp-lasiRNA (survivin) structures.

<cp-lasiRNA (survivin)>

```
cp-lasiRNA (survivin) Antisense 31 nt:
                              (SEQ ID NO: 169)
5' UGAAAAUGUUGAUCUCCUUUCCUAAGA*C*A*T*T 3'
```

-continued
```
cp-1asiRNA (survivin) Sense:
                                       (SEQ ID NO: 170)
5' GAGAUCAACAUUUU*C*A*cholesterol. 3'
```

Underline: OMe modification, *: PS (phosphorothioate bond or phosphorodithioate bond)

As a result, as can be seen in FIG. 11, an increase in the gene silencing effect by additional sulfur modification (PS2) was not observed, and the cp-lasiRNA structure having PS2 modification showed reduced gene silencing efficiency compared to the conventional cp-lasiRNA.

Example 7: Measurement of In Vivo Target Gene Silencing Efficiency of Nucleic Acid According to the Present Invention In the current development of therapeutic agents based on RNAi technology, the development of effective in vivo RNA delivery technology is most difficult. Many delivery technologies developed to date show high in vitro delivery efficiency, but have a problem in that, when these are applied in vivo, the efficiency thereof significantly decreases. Thus, in order to examine whether the nucleic acid molecule according to the present invention has a high gene silencing effect even in vivo, cp-lasiRNA alone was injected into the skin of rats without using a separate delivery vehicle, and the target gene silencing effect thereof was measured.

Figure 12:
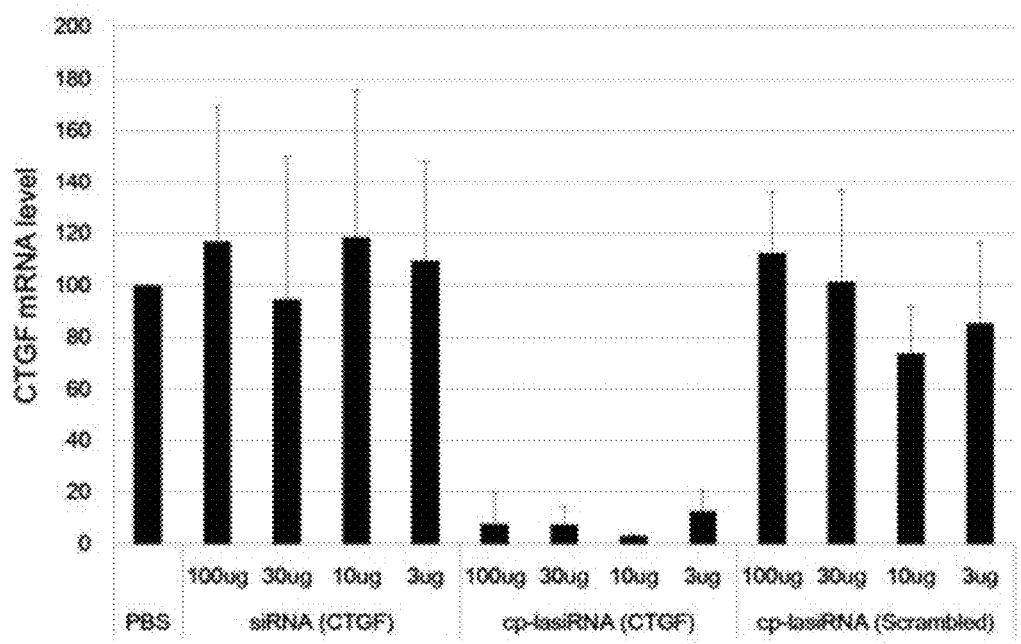
FIG. 12 is a graphic diagram showing the in vivo target gene silencing efficiencies of the nucleic acid molecules according to the present invention.

Specifically, siRNA (CTGF), cp-lasiRNA (CTGF) or cp-lasiRNA (Scrambled) was dissolved in 100 μl of PBS at concentrations shown in FIG. 12, and each of the solutions was injected intradermally into the rat skin, and after 24 hours, the skin tissue was collected, and the expression of the target gene therein was measured. Specifically, SD rats (Orient Bio Inc.) were anesthetized by intraperitoneal injection with Zoletil and Rompun solution, and then the back of the rats was shaved. A circle having a radius of 5 mm was drawn on the shaved skin portion, and then 100 μl of PBS, siRNA or cp-lasiRNA was injected intradermally into the central portion of the circle by an insulin syringe (BD, 31G). After injection, the skin tissue was taken using 8 mm biopsy punch at the indicated date, and the expression of gene therein was analyzed. The nucleic acids used are as follows.

```
cp-1asiRNA (CTGF) Antisense Rat:
                                       (SEQ ID NO: 177)
5'- UCUUCCAGUCGGUAGGCAGCUAGGGCA*G*G*G*C -3' cp-1asiRNA (CTGF) Sense Rat:
                                       (SEQ ID NO: 178)
5'- CCTACCGACTGGAA*G*A*choleterol. 3'
```

Underline: OMe modification, *: PS (phosphorothioate bond)

The followings were used as siRNA:

```
siRNA (CTGF) antisense:
                                       (SEQ ID NO: 179)
5'- CUGCCUACCGACUGGAAGATT -3' siRNA (CTGF) sense:
                                       (SEQ ID NO: 180)
5'- CUGCCUACCGACUGGAAGATT -3'
```

Underline: OMe modification

Herein, RNA was extracted using an RNeasy fibrous tissue mini kit (Qiagen), and 1 μg of the RNA was used for cDNA synthesis. cDNA was synthesized using a high-capacity cDNA reverse transcription kit (Applied Biosystems) according to the protocol provided therein. The synthesized cDNA was diluted, and then subjected to quantitative real-time PCR using a step one real-time PCR system (Applied Biosystems) according to the protocol provided therein. The target gene was analyzed using a power SYBR green PCR master mix (Applied Biosystems) together with gene-specific primers. The nucleotide sequences of the primers used in the experiment are as follows. Each graph in FIG. 12 represents the mean±SD of five repeated experiments.

CTGF-Rat

```
Forward
                                       (SEQ ID NO: 181)
5'-GGC TCG CAT CAT AGT TG-3'

Reverse
                                       (SEQ ID NO: 182)
5'-CGG GAA ATG CTG TGA GGA GT-3'
``` siRNA (CTGF), cp-lasiRNA (CTGF) or cp-lasiRNA (Scrambled) was dissolved in 100 μl of PBS at the indicated concentrations, and each of PBS and the solutions was injected intradermally into the rat skin, and after 24 hours, the skin tissue was collected, and the expression of the target gene therein was measured. Each graph in FIG. 12 represents the mean±SD of five repeated experiments.

As a result, as can be seen in FIG. 12, the expression of CTGF in the group treated with cp-lasiRNA (CTGF) decreased by 80-90% or higher compared to that in the group treated with PBS, cp-lasiRNA (scrambled) or siRNA (CTGF), suggesting that cp-lasiRNA can highly efficiently silence the target gene even in vivo.

Additionally, in order to examine the in vivo gene silencing efficiency of Cp-lasiRNA, cp-lasiRNA was injected into rats at a concentration ranging from 100 μg/injection to 0.1 μg/injection in the same manner as described above, and then the expression of the target gene was measured.

Figure 13:
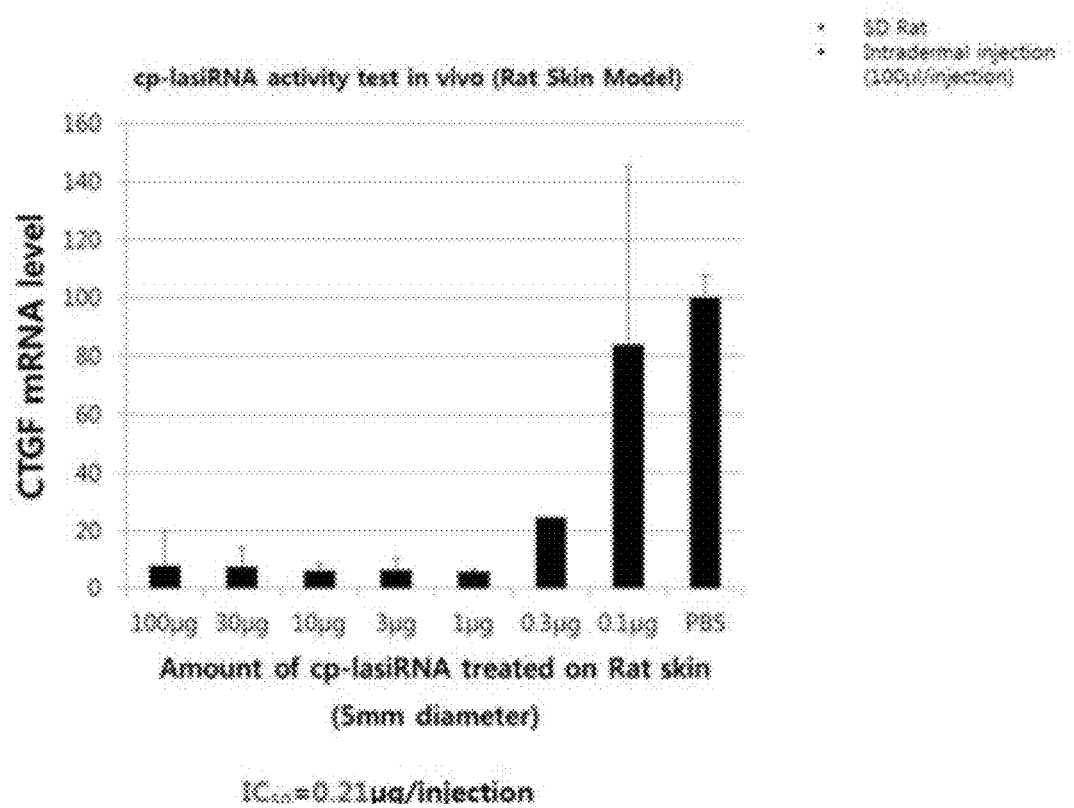
FIG. 13 is a graphic diagram showing the in vivo target gene silencing efficiency of the inventive nucleic acid molecule as a function of the concentration thereof.

As a result, as shown in FIG. 13, cp-lasiRNA (CTGF) showed a target gene silencing efficiency of 70% or higher even at a low concentration of about 0.3 μg/injection, and had an IC50 value of about 0.21 μg/injection. Each graph in FIG. 13 represents the mean±SD of two repeated experiments.

Additionally, cp-lasiRNA (CTGF) was injected in the same manner as described above, and then on day 1, day 2, day 3 and day 6, the tissue was analyzed to measure the expression of the gene. cp-lasiRNA (CTGF) was injected intradermally, after which the tissue was collected at the indicated date, and the expression of CTGF therein was analyzed by real-time PCR.

Figure 14:
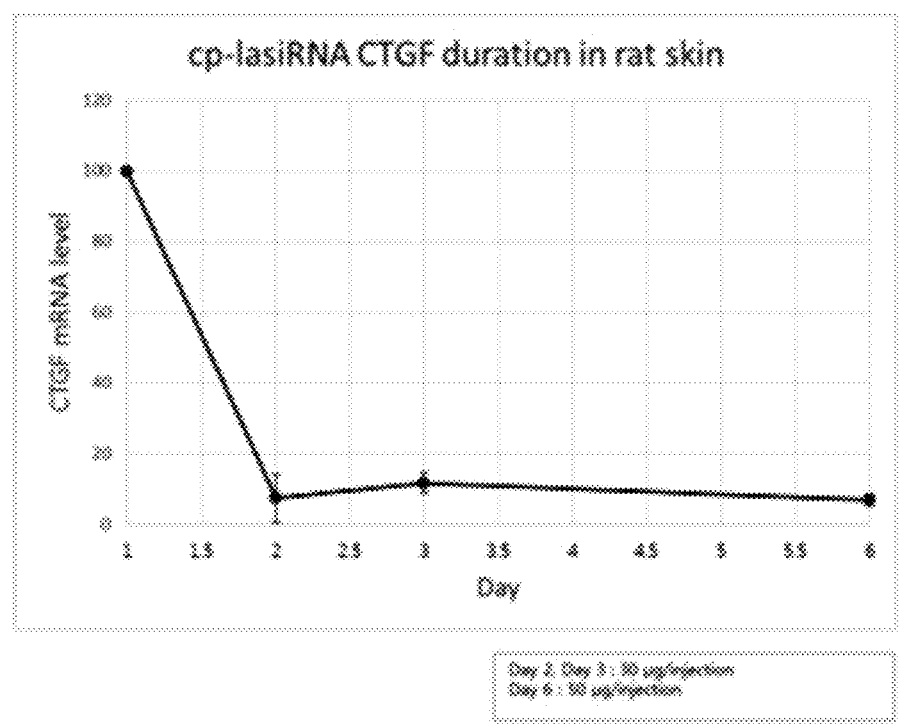
FIG. 14 is a graphic diagram showing the target gene silencing efficiency of the inventive nucleic acid molecule as a function of duration.

As a result, as shown in FIG. 14, it was found that cp-lasiRNA (CTGF) silenced the target gene for at least 5 days. Each graph in FIG. 14 represents the mean±SD of two repeated experiments.

INDUSTRIAL APPLICABILITY

As described above, the nucleic acid structure according to the present invention has both cholesterol modification and phosphorothioate modification introduced therein, and thus has high gene silencing efficiency while having the ability to penetrate cells without needing a separate intracellular delivery vehicle. Thus, it can be delivered into an actual target area in an amount sufficient for induction of RNAi, and thus can overcome the in vivo delivery problem occurring in the prior art. Therefore, the nucleic acid molecule according to the present invention can effectively substitute for conventional siRNA molecules to treat cancer or viral infections.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. An RNAi-inducing double-stranded nucleic acid molecule comprising:
   a first strand having a nucleotide sequence consisting of the nucleotide sequence of SEQ ID NO: 154 and comprising 4 to 17 phosphorothioate bonds and at least one 2'-O-Me modified nucleotide; and
   a second strand having a nucleotide sequence consisting of the nucleotide sequence of SEQ ID NO: 153 and comprising at least one phosphorothioate bond and at least one 2'-O-Me modified nucleotide and further comprising a cholesterol moiety covalently attached to its 3' end;
   wherein the second strand binds to the first strand such that the first strand has a double-stranded region to which the second strand binds and a single-stranded region to which the second strand does not bind, and wherein the 5' end of the first strand and the 3' end of the second strand form a blunt end.

2. The nucleic acid molecule of claim 1, wherein at least one of the nucleotides of the single-stranded region in the first strand comprises a deoxyadenosine derivative having a phenyl group.

3. A gene-silencing composition comprising the nucleic acid molecule according to claim 1 and a pharmaceutically acceptable carrier, excipient or diluent.

4. The nucleic acid molecule of claim 1, wherein the first strand comprises 7 to 12 phosphorothioate bonds.

5. The nucleic acid molecule of claim 1, wherein the 4 to 17 phosphorothioate bonds are the 4 to 17 internucleotide bonds located closest to the 3' end of the first strand of the nucleic acid molecule.

6. The nucleic acid molecule of claim 4, wherein the 7 to 12 phosphorothioate bonds are the 7 to 12 internucleotide bonds located closest to the 3' end of the first strand of the nucleic acid molecule.

7. The nucleic acid molecule of claim 1, wherein the first strand comprises 2'-O-Me modified nucleotides at positions 1, 9, 11, 13, 15, 17, 19, 21, 23, 25, 27, 29 and 31 of SEQ ID NO: 154.

8. The nucleic acid molecule of claim 1, wherein the second strand comprises 2'-O-Me modified nucleotides at positions 1, 3, 5, 7, 9, 11, 13 and 15 of SEQ ID NO: 153.

9. The nucleic acid molecule of claim 7, wherein the second strand comprises 2'-O-Me modified nucleotides at positions 1, 3, 5, 7, 9, 11, 13 and 15 of SEQ ID NO: 153.

10. The nucleic acid molecule of claim 1, wherein the second strand comprises three phosphorothioate bonds.

11. The nucleic acid molecule of claim 10, wherein the cholesterol moiety is covalently attached to the 3' end of the second strand by an additional phosphorothioate bond.

12. The nucleic acid molecule of claim 11, wherein the three phosphorothioate bonds are the two internucleotide bonds located closest to the 3' end of the second strand of the nucleic acid molecule and the covalent bond that attaches the cholesterol moiety to the 3' end of the second strand of the nucleic acid molecule.

13. The nucleic acid molecule of claim 9, wherein the second strand comprises three phosphorothioate bonds.

14. The nucleic acid molecule of claim 13, wherein the cholesterol moiety is covalently attached to the 3' end of the second strand by an additional phosphorothioate bond.

15. The nucleic acid molecule of claim 14, wherein the three phosphorothioate bonds are the two internucleotide bonds located closest to the 3' end of the second strand of the nucleic acid molecule and the covalent bond that attaches the cholesterol moiety to the 3' end of the second strand of the nucleic acid molecule.

* * * * *